US006214821B1

(12) United States Patent
Daoud

(10) Patent No.: US 6,214,821 B1
(45) Date of Patent: Apr. 10, 2001

(54) METHODS AND COMPOSITION FOR THE INHIBITION OF CANCER CELLS

(75) Inventor: Sayed S. Daoud, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/262,452

(22) Filed: Mar. 4, 1999

Related U.S. Application Data
(60) Provisional application No. 60/076,960, filed on Mar. 5, 1998.

(51) Int. Cl.$^7$ ............................ A61K 31/55; A61K 31/44

(52) U.S. Cl. ...................... 514/214.02; 514/283

(58) Field of Search ............................... 514/283, 214.02, 514/214

(56) References Cited

U.S. PATENT DOCUMENTS

| 4,342,776 | 8/1982 | Cragoe, Jr. et al. ................. 424/274 |
| 4,399,276 | 8/1983 | Miyasaka et al. .................... 542/416 |
| 4,473,692 | 9/1984 | Miyasaka et al. ...................... 546/48 |
| 4,513,138 | 4/1985 | Miyasaka et al. ...................... 546/48 |
| 4,545,880 | 10/1985 | Miyasaka et al. ............... 204/158 R |
| 4,604,463 | 8/1986 | Miyasaka et al. .................... 544/125 |
| 4,935,415 | 6/1990 | Nakano et al. ....................... 514/211 |
| 5,004,758 | 4/1991 | Boehm et al. ........................ 514/283 |
| 5,786,344 | * 7/1998 | Ratain et al. ......................... 514/211 |

FOREIGN PATENT DOCUMENTS

| 0 088 642 A2 | 9/1983 | (EP) . |
| 0 321 122 B1 | 6/1989 | (EP) . |
| 0 418 099 A2 | 3/1991 | (EP) . |

OTHER PUBLICATIONS

Shao et al., Cancer Res., 57(18), 4029–4035 Abstract Only, 1997.*
Akinaga et al., "Antitumor Activity of UCN–01, a Selective Inhibitor of Protein Kinase C, in Murine and Human Tumor Models," *Cancer Res.* 51:4888–4892 (1991).
Barlogie, Barthel and Benjamin Drewinko, "Cell Cycle Stage–Dependent Induction of $G_2$ Phase Arrest by Different Antitumor Agents," *Europ. J. Cancer* 14:741–745 (1978).
Bunch, Roderick T. and Alan Eastman, "Enhancement of Cisplatin–induced Cytotoxicity by 7–Hydroxystaurosporine (UCN–01), a New $G_2$–Checkpoint Inhibitor," *Clinical Cancer Res.* 2:791–797 (1996).
Chou, Ting–Chao and Paul Talalay, "Quantitative analysis of dose–effect relationships: The combined effects of multiple drugs or enzyme inhibitors," *Adv. Enzyme Regul.* 22:27–55 (1984).
Clements et al., "Antiangiogenic potential of camptothecin and topotecan," *Cancer Chemother Pharmacol* 44:411–416 (1999).

Dancey, J. and E.A. Eisenhauer, "Current perspectives on campthothecins in cancer treatment." *Br. J. Cancer* 74:327–338 (1996).
Daoud, Sayed S. and N.H. Forde, "Synergistic cytotoxic actions of cisplatin and liposomal valinomycin on human ovarian carcinoma cells," *Cancer Chemother. Pharmacol.* 28:370–376 (1991).
Daoud, Sayed S. and R.L. Juliano, "Modulation of Doxorubicin Resistance by Valinomycin (NSC 122023) and Liposomal Valinomycin in Chinese Hamster Ovary Cells," *Cancer Res.* 49:2661–2667 (1989).
Daoud et al., "Antitumor effect of liposome–incorporated camptothecin in human malignant xenografts," *Anti–Cancer Drugs* 6:83–93 (1995).
Daoud, S.S., "Combination chemotherapy of human ovarian xenografts in intraperitoneal liposome–incorporated valinomycin and cis–diamminedichloroplatinum(II)," *Cancer Chemother Pharmacol* 33:307–312 (1994).
D'Apra et al., "Involvement of Nucleic Acid Synthesis in Cell Killing Mechanisms of Topoisomerase Poisons," *Cancer Res.* 50:6919–6924 (1990).
Darzynkiewicz et al., "The Cell Cycle Effects of Camptothecin." In: Pantazis, P., Giovanella, B.C., Rothenberg, M.L (eds.), *The camptothecins from discovery to the patient.* The New York Academy of Sciences, New York, 803:93–101 (1996).
du Souich et al., "Plasma Protein Binding and Pharmacological Response," *Clin. Pharmacokinet* 24:435–440 (1993).
Dubrez et al., "The role of cell cycle regulation and apoptosis triggering in determining the sensitivity of leukemia cells to topoisomerase I and II inhibitors," *Leukemia* 9:1013–1014 (1995).
Fan et al., "p53 Gene Mutations are Associated with Decreased Sensitivity of Human Lymphoma Cells to DNA Damaging Agents," *Cancer Res.* 54:5824–5830 (1994).
Fan et al., Disruption of p53 Function Sensitizes Breast Cancer MCF–7 Cells to Cisplatin and Pentoxifylline, *Cancer Res.* 55:1649–1654 (1995).
Foster et al., "The Ability of Human Papillomavirus E6 Proteins to Target p53 for Degradation In Vivo Correlates with Their Ability to Abrogate Actinomycin D–Induced Growth Arrest," *J. Virol.* 68:5698–5705 (1994).

(List continued on next page.)

*Primary Examiner*—Jerome D. Goldberg
(74) *Attorney, Agent, or Firm*—Christensen O'Connor Johnson Kindness PLLC

(57) ABSTRACT

Pharmaceutical compositions comprising a topoisomerase I inhibitor, such as camptothecin or a camptothecin analog, and a staurosporine such as 7-hydroxystaurosporine, together with a pharmaceutically acceptable carrier or diluent are provided. In other aspects, methods of inhibiting the growth of cancer cells are provided by contacting the cells with an cell growth inhibiting amount of a topoisomerase I inhibitor, such as camptothecin or a camptothecin analog, and a staurosporine, such as 7-hydroxystaurosporine, while protecting normal cells from topoisomerase I inhibitor induced cytotoxicity.

10 Claims, 18 Drawing Sheets

OTHER PUBLICATIONS

Goldwasser et al., "Correlations between S and $G_2$ Arrest and the Cytotoxicity of Camptothecin in Human Colon Carcinoma Cells," *Cancer Res.* 56:4430–4437 (1996).

Hartwell, Leland H. and Ted. A. Weinert, "Checkpoints: Controls That Ensure the Order of Cell Cycle Events," *Science* 246:629–634 (1989).

Jones et al., "Sensitivity to camptothecin of human breast carcinoma and normal endothelial cells," *Cancer Chemother. Pharmacol.* 40:475–483 (1997).

Jones et al., "Synergy between UCN–01 and camptothecin–induced cytotoxicity in breast cancer cells," *Proc. AACR* 38:abstract 102 (1997).

Kastan et al., "Participation of p53 Protein in the Cellular Response to DNA Damage," *Cancer Res.* 51:6304–6311 (1991).

Knowlton et al., "Bcl–2 Slows in Vitro Breast Cancer Growth Despite Iits Antiapoptotic Effect," *J. Surg. Res.* 76:22–26, 1998.

Kuerbitz et al., "Wild–type p53 is a cell cycle checkpoint determinant following irradiation," *Proc. Natl. Acad. Sci. USA* 89:7491–7495 (1992).

Lane, D.P., "p53, guardian of the genome," *Nature* (Lond.) 358:15–16 (1992).

Lee, Jonathan M. and Alan Bernstein, "p53 mutations increase resistance to ionizing radiation," *Proc. Natl. Acad. Sci. USA* 90:5742–5746 (1993).

Lowe et al., "p53 Status and the Efficacy of Cancer Therapy in Vivo," *Science* 266:807–810 (1994).

Lush et al., "Surprising pharmacokinetics of UCN–01 in patients with refractory neoplasms may be due to high degree of protein binding," *Proc. AACR* 38:600, abstract 4029 (1997).

Monks et al., "Synergistic interactions between UCN–01 and various anti–cancer agents in vitro: Relationship to p53 function," *Proc. AACR* 38:322, abstract 2157 (1997).

O'Connor et al., "S–Phase Population Analysis Does Not Correlate with the Cytotoxicity of Camptothecin and 10,11–Methyldioxycamptothecin in Human Colon Carcinoma HT–29 Cells," *Cancer Commun.* 3:233–240 (1991).

Peacock et al., "The p53–Mediated $G_1$ Checkpoint is Retained in Tumorigenic Rat Embryo Fibroblast Transformed by the Human Papillomavirus Type 16 E7 Gene and EJ–ras," *Mol. Cell Biol.* 15:1446–1454 (1995).

Pines, J., "Cyclins, CDKs and Cancer," *Semin. Cancer Biol.* 6:63–72 (1995).

Powell et al., "Differential Sensitivity of p53(–) and p53(+) Cells to Caffeine–induced Radiosensitization and Override of $G_2$ Delay," *Cancer Res.* 55:1643–1648 (1995).

Riabowol et al., "The cdc2 Kinase Is a Nuclear Protein That Is Essential for Mitosis in Mammalian Cells," *Cell* 57:393–401 (1989).

Redkar, A.A. and S.S. Daoud, "UCN–01 dose–dependent protective effect of normal tissue in mice," *Proc. AACR* 40:11, abstract 70 (1999).

Russell et al., "Abrogation of the $G_2$ Checkpoint Results in Differential Radiosensitization of $G_1$ Checkpoint–deficient and Checkpoint–competent Cells," *Cancer Res.* 55:1639–1642 (1995).

Ryan et al., "Camptothecin cytotoxicity in mammalian cells is associated with the interaction of persistent double strand breaks in replicating DNA," *Nucleic Acid Res.* 19:3295–3300 (1991).

Seynaeve et al., "Cell Cycle Arrest and Growth Inhibition by the Protein Kinase Antagonist UCN–01 in Human Breast Carcinoma Cells," *Cancer Res.* 53:2081–2086 (1993).

Shao et al., "Abrogation of an S–Phase Checkpoint and Potentiation of Camptothecin Cytotoxicity by 7–Hydroxystaurosporine (UCN–01) in Human Cancer Cell Lines, Possibly Influenced by p53 Function," *Cancer Res.* 57:4029–4035 (1997).

Shao et al., "Potentiation of comptothecin cytotoxicity in p53 mutant HT–29 cells by UCN–01, an abrogator of the S and G2 checkpoints," *Proc. AACR* 38:439, abstract 2938 (1997).

Sinha, B.K., "Topoisomerase Inhibitors: A review of their Therapeutic Potential in Cancer," *Drugs* 49:11–19 (1995).

Sorenson, Christine M. and Alan Eastman, "Mechanism of cis–Diamminedichloroplatinum(II)–induced Cytotoxicity: Role of $G_2$ Arrest and DNA Double–Strand Breaks," *Cancer Res.* 48:4484–4488 (1988).

Strausfeld et al., "Dephosphorylation and activation of a $p34^{cdc2}$/cyclin B complex in vitro by human CDC25 protein," *Nature* 351:242–244 (1991).

Takahashi et al., "UCN–01, a selective inhibitor of protein kinase C from Streptomyces," *J. Antibiot.* 40:1782–1784 (1987).

Tsao et al., "The Involvement of Active DNA Synthesis in Camptothecin–induced $G_2$ Arrest: Altered Regulation $p34^{cdc2}$/Cyclin B," *Cancer Res.* 52:1823–1829 (1992).

Wang et al., "UCN–01: a Potent Abrogator of $G_2$ Checkpoint Function in Cancer Cells with Disrupted p53," *JNCI* 88:956–965 (1996).

Wang et al., "Apoptosis in 7–Hydroxystaurosporine–treated T Lymphoblasts Correlates with Activation of Cyclin–dependent Kinase 1 and 2," *Cell Growth Differ.* 6:927–936 (1995).

Wang et al., "Down–Regulation of DNA Replication in Extracts of Camptothecin–treated Cells: Activation of an S–phase Checkpoint?," *Cancer Res.* 57:1654–1659 (1997).

\* cited by examiner

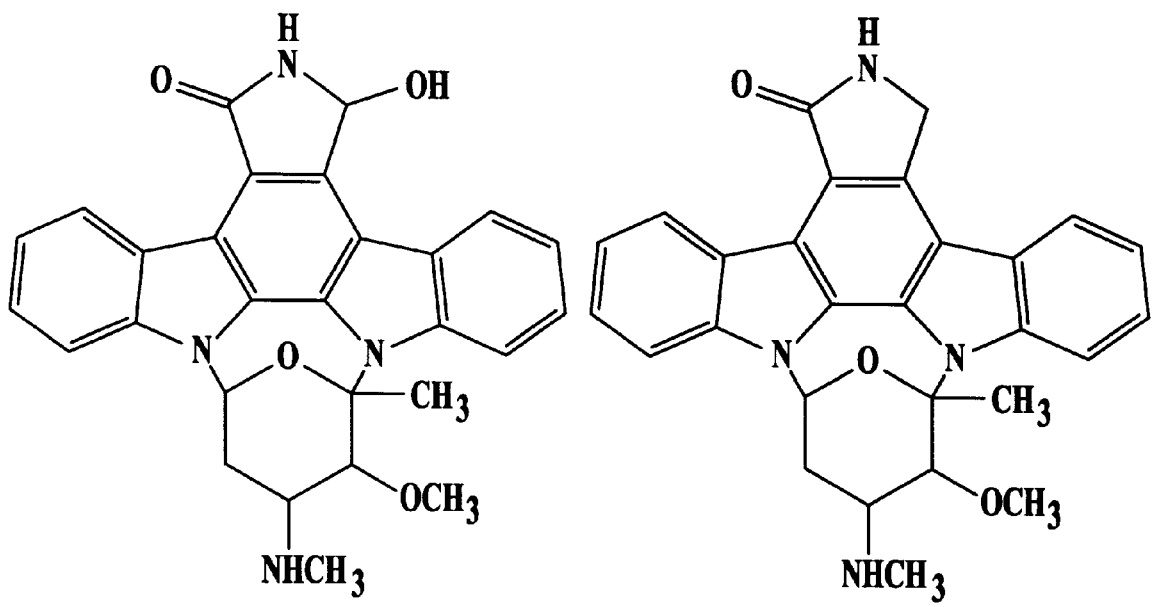
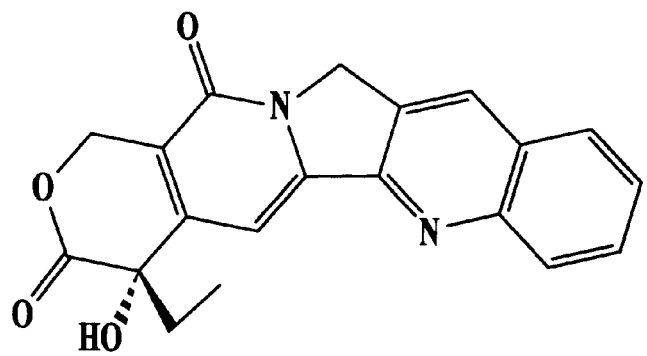
Fig. 1

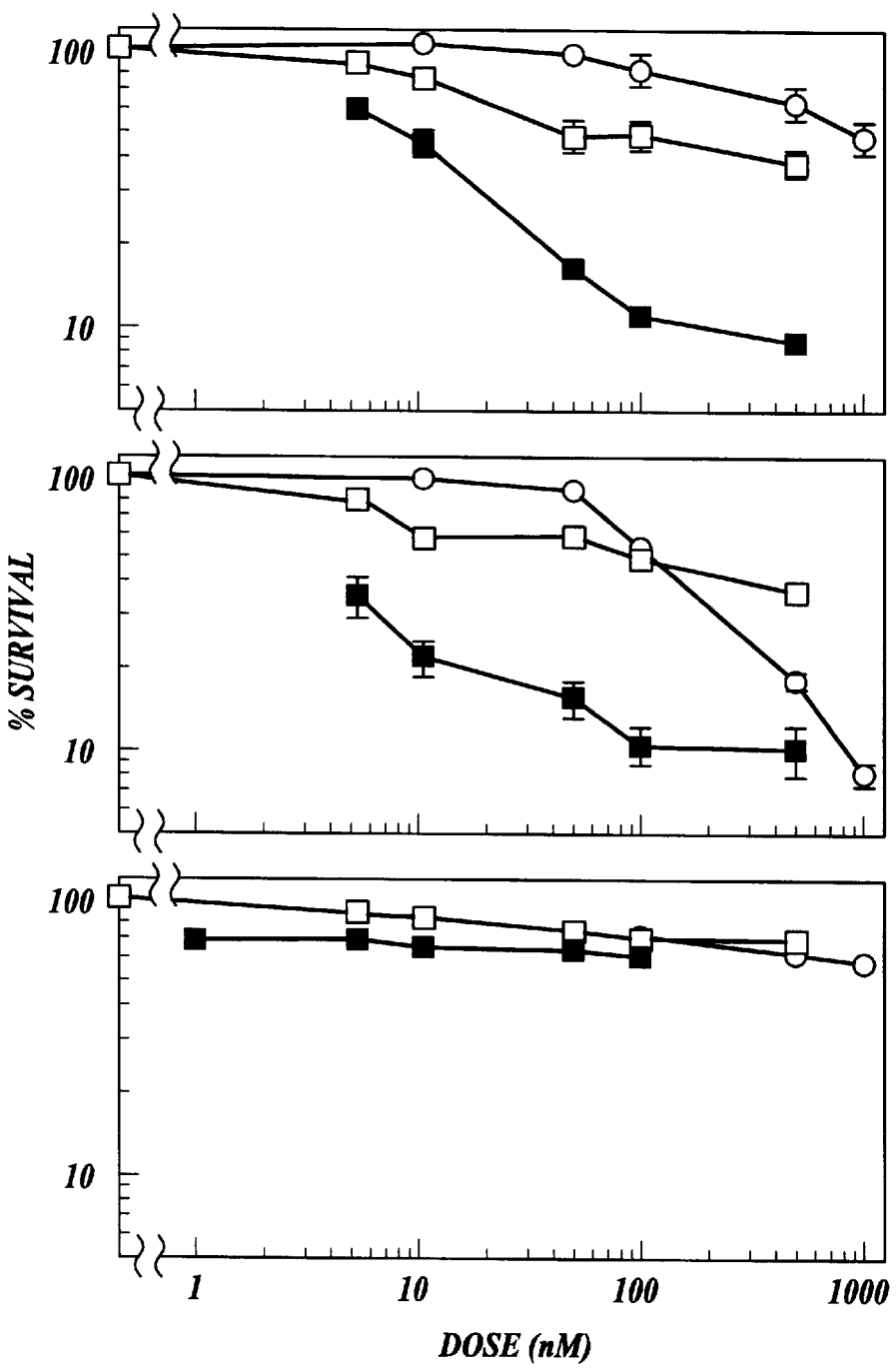

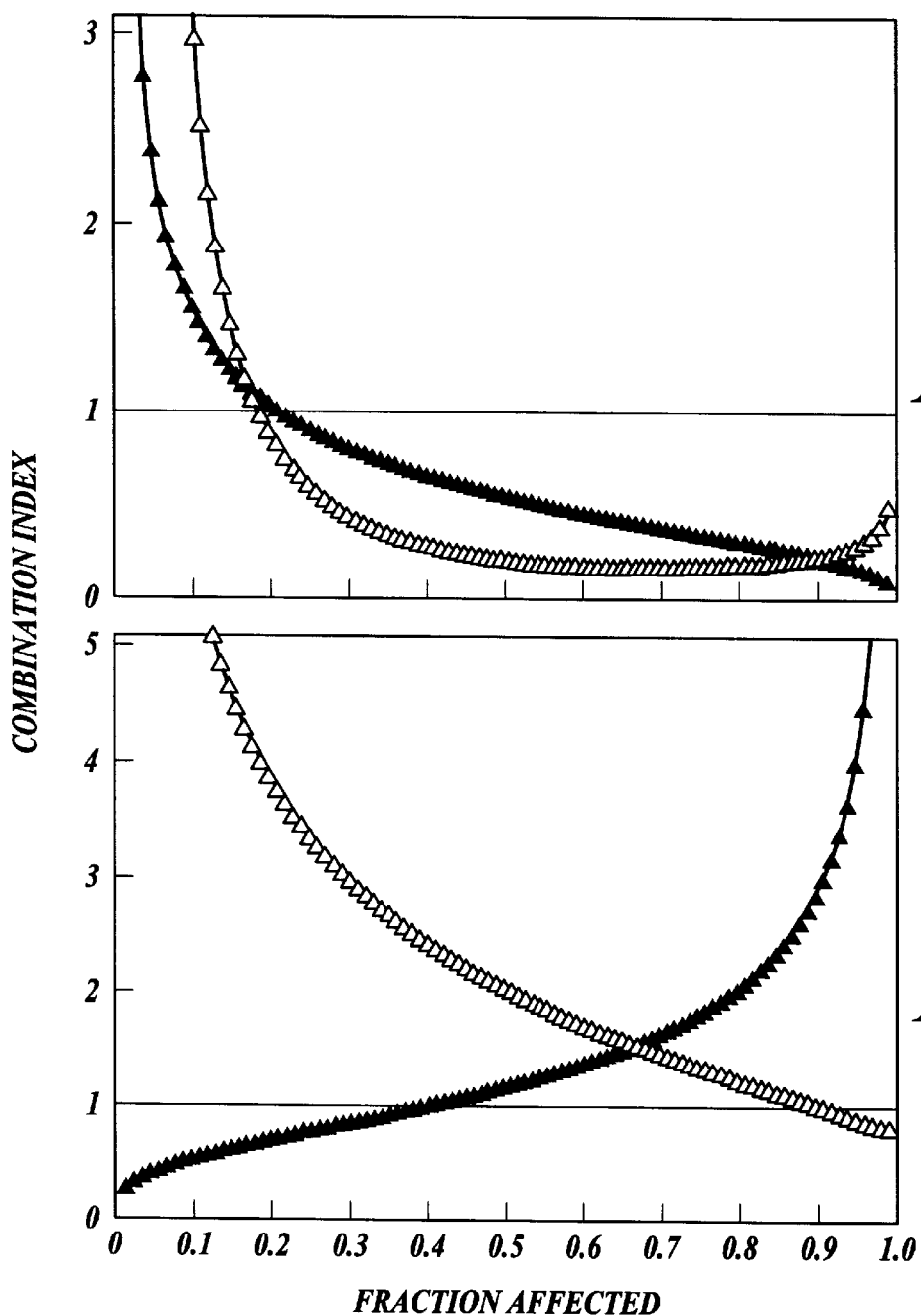

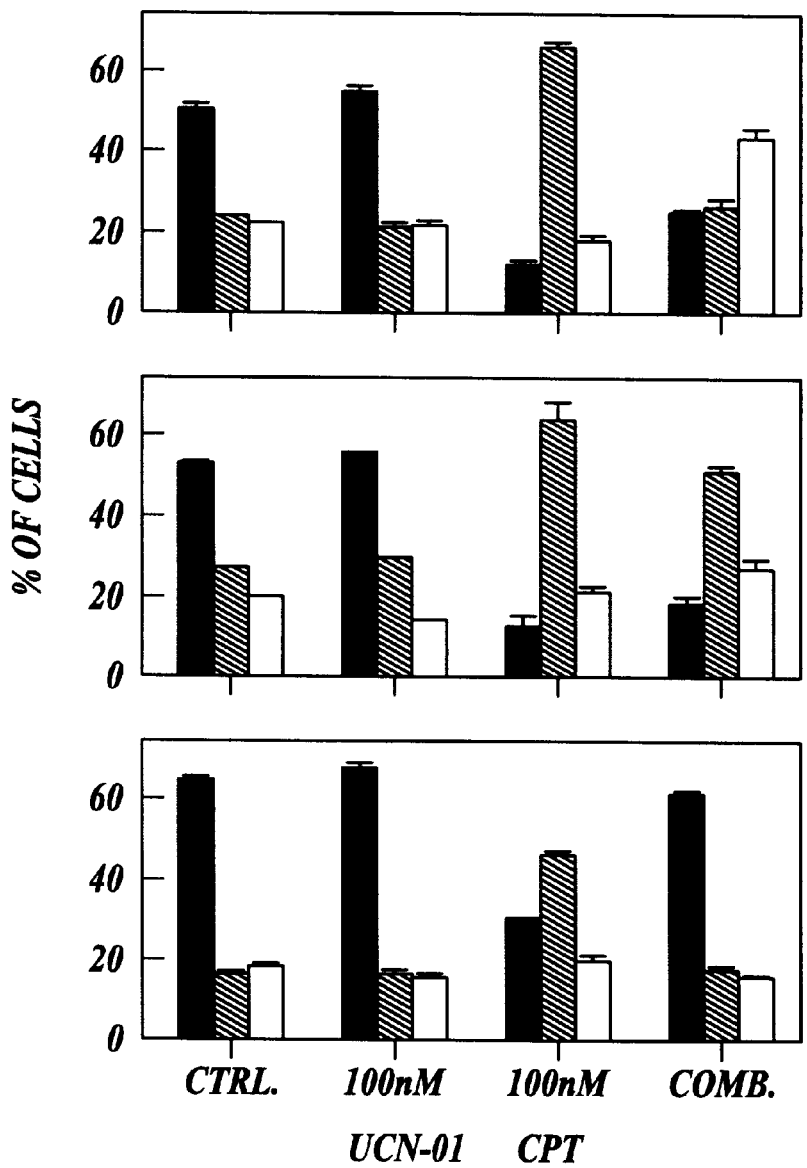

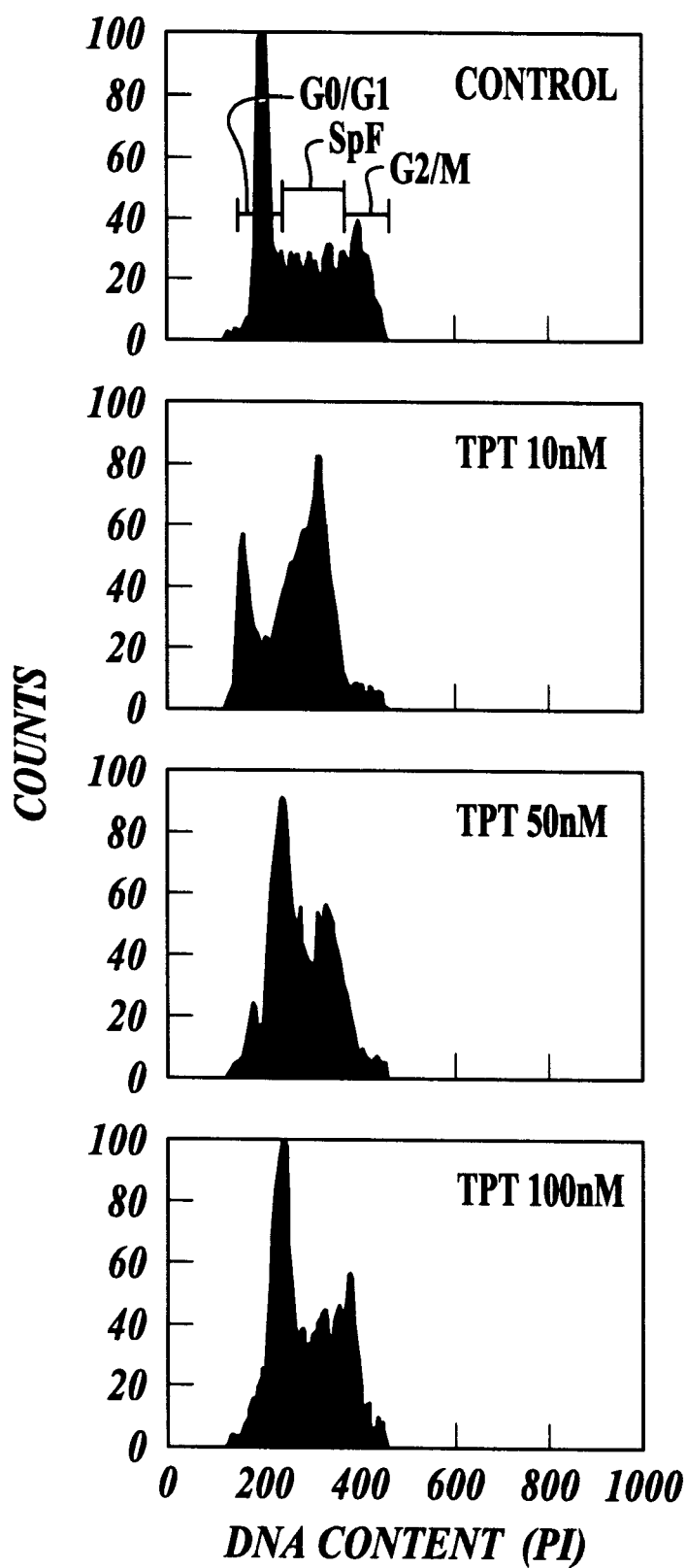

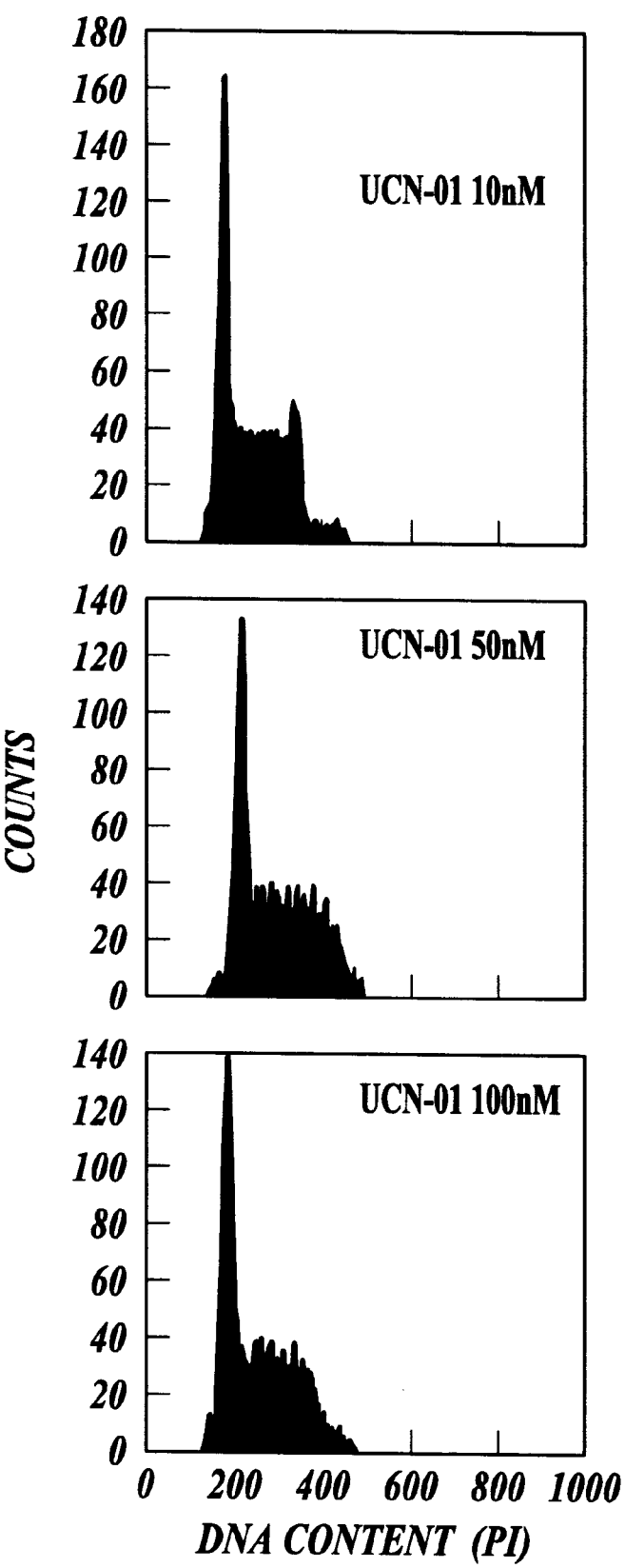

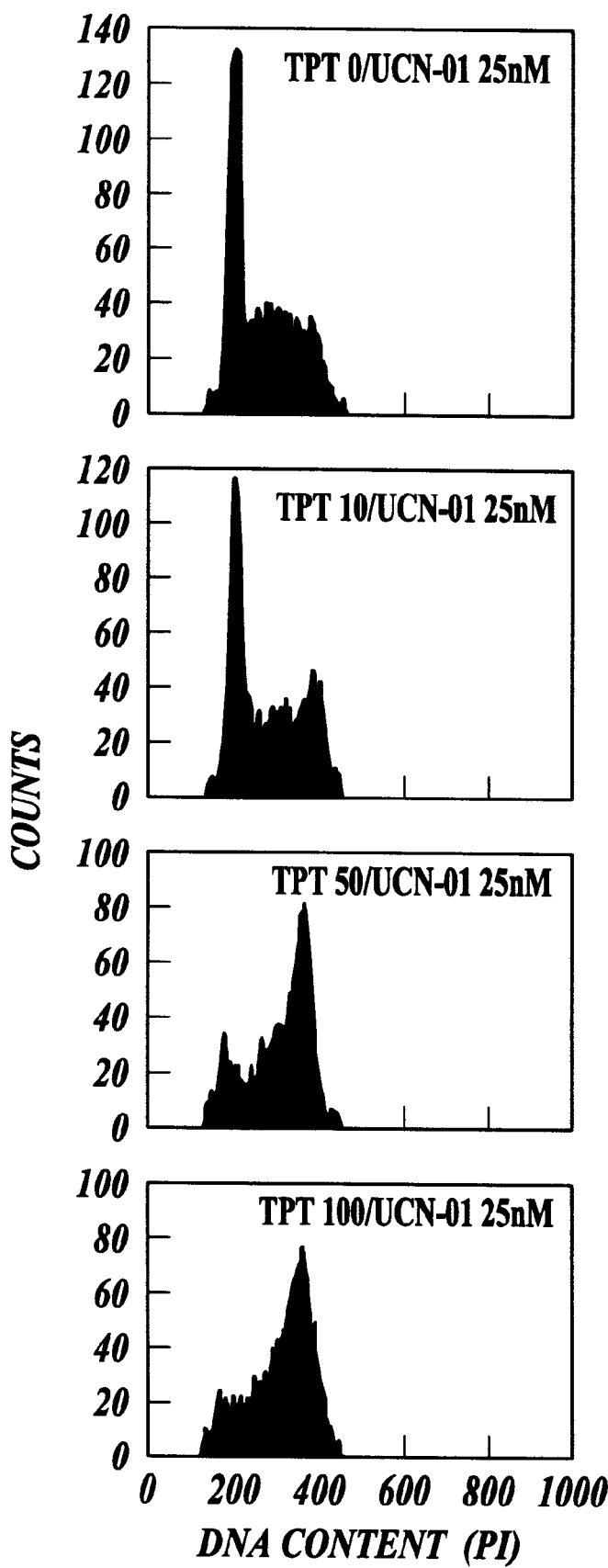

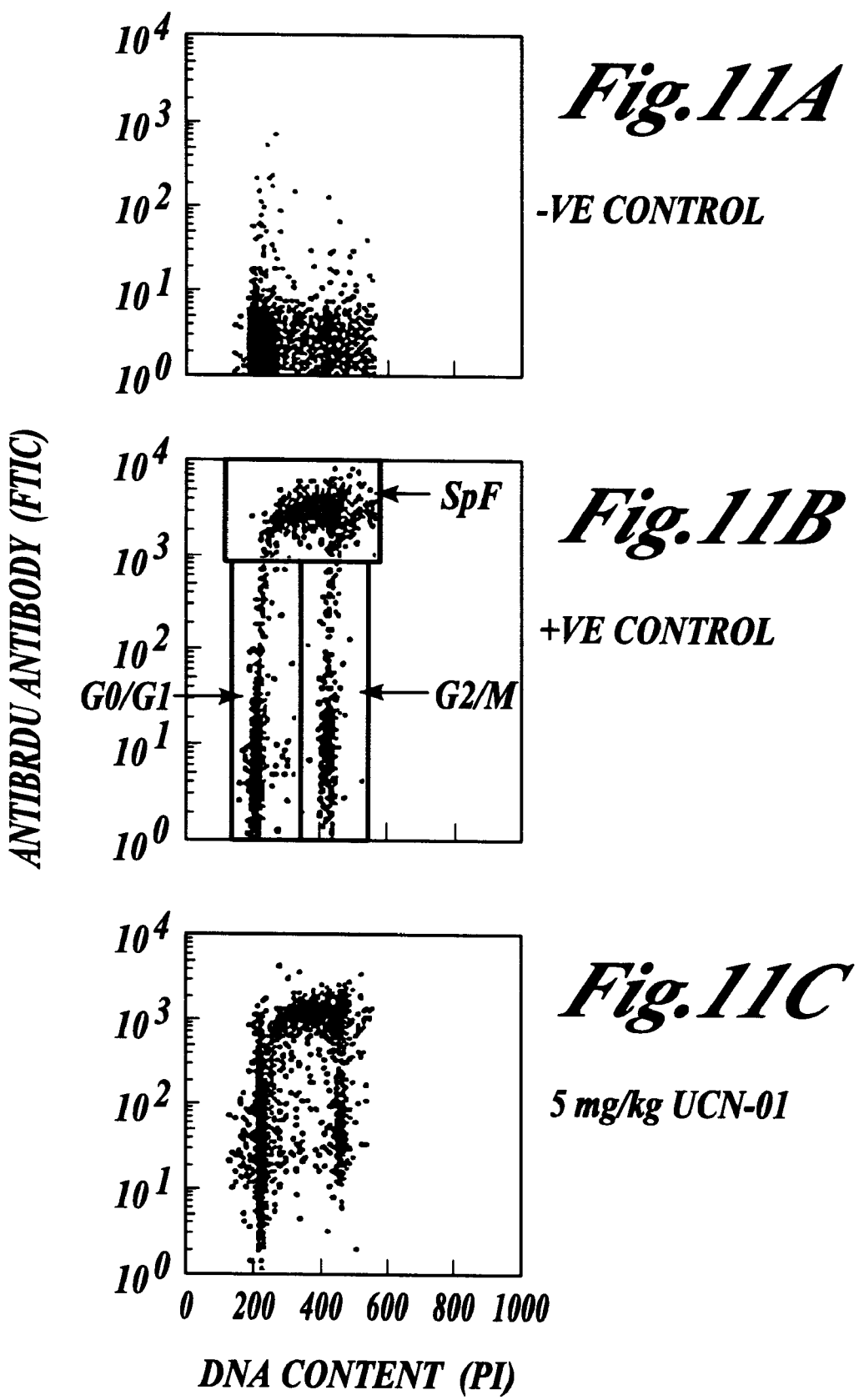

METHODS AND COMPOSITION FOR THE INHIBITION OF CANCER CELLS

This application claims the benefit of U.S. Provisional Application No. 60/076,960 filed Mar. 5, 1998.

FIELD OF THE INVENTION

The present invention relates to pharmaceutical compositions comprising a topoisomerase I inhibitor and a staurosporine. The invention also relates to methods of inhibiting the growth of cancer cells with a composition of the invention while protecting normal cells from the adverse effects of topoisomerase I inhibitor therapy. In other aspects, the invention relates to methods of achieving enhanced concentrations of topoisomerase I inhibitors in the presence of staurosporine.

BACKGROUND OF THE INVENTION

Camptothecin (CPT) and its clinical analogs such as topotecan (TPT) and CPT-11 are a new class of chemotherapeutic agents with a novel mechanism of action targeting the nuclear enzyme topoisomerase I (topoisomerase), causing single and double strand-DNA breaks and subsequent cell death (for reviews, see Dancey J. et al. "Current perspectives on camptothecins in cancer treatment." *Br. J. Cancer* 74:327–338 (1996) and Sinha B. K., "Topoisomerase I inhibitors: A review of their therapeutic potential in cancer," *Drugs* 49:11–16 (1995)). The cytotoxicity of these agents is predominantly exerted during the S phase of the cell cycle (Darzynkiewicz Z. et al., "The cell cycle effects of camptothecins." In: Pantazis P. et al. (eds)., *The camptothecins from discovery to the patient*, The New York Academy of Sciences, New York, vol. 803, pp. 93–101 (1996)). This inhibition is the result of a passive collision of the advancing DNA replication forks with the CPT-topoisomerase-DNA cleavable complexes which are expected to cause an arrest of DNA replication and to kill cells by generating DNA strand breaks (D'Apra P. et al., "Involvement of nucleic acid synthesis in cell killing mechanisms of topoisomerase poisons." *Cancer Res.* 50:6919–6924 (1990) and Ryan A. J. et al., "Camptothecin cytotoxicity in mammalian cells is associated with the interaction of persistent double strand breaks in replicating DNA," *Nucleic Acid Res.* 19:3295–3300 (1991)).

The sensitivity of cells to CPT and its analogs can not be completely explained by the collision model. Recent evidence has indicated that the sensitivity of cells to CPT is also determined by their ability to activate checkpoints in the S and $G_2$ phases of the cell cycle (Jones C. B. et al., "Sensitivity to camptothecin of human breast cancer cells and normal bovine endothelial cells, in vitro," *Cancer Chemother. Pharmacol.* (in press, 1997); O'Connor P. M. et al., "S-phase population analysis does not correlate with the cytotoxicity of camptothecin and 10,11-methyldioxycamptothecin in human colon carcinoma HT-29 cells," *Cancer Commun.* 3:233–240 (1991); Dubrez L. et al., "The role of cell cycle regulation and apoptosis triggering in determining the sensitivity of leukemia cells to topoisomerase I and II inhibitors," *Leukemia* 9:1013–1024 (1995); Wang Y. et al., "Down-regulation of DNA replication in extracts of camptothecin-treated cells: Activation of an S-phase checkpoint," *Cancer Res.* 57:1654–1659 (1997); and Goldwasser F. et al., "Correlations between S and $G_2$ arrest and the cytotoxicity of camptothecin in human colon carcinoma cells," *Cancer Res.* 56:4430–4437 (1996)). This activation in S phase occurs with high doses of CPT and $G_2/M$ when low doses of CPT are used, presumably to avoid high and low levels of DNA damage, respectively. DNA damage extends the time of at least two stages or checkpoints in the cell cycle, the $G_1$-S and the $G_2$-M transitions (Hartwell L. H. et al., "Checkpoints: controls that ensure the order of the cell cycle events," *Science* 246:629–634 (1989)). A critical component of the $G_1$ checkpoint is the p53 gene product, which when inactivated by mutations, renders a cell incapable of $G_1$ arrest following DNA damage (Kastan M. B. et al., "Participation of p53 protein in the cellular response to DNA damage," *Cancer Res.* 51:6304–6311 (1991); and Kuerbitz S. J. et al., "Wild-type p53 is a cell cycle checkpoint determinant following irradiation," *Proc. Natl. Acad. Sci. USA* 89:7491–7495 (1992)). Instead, cells arrest in $G_2$ phase, (Barlogie B. et al., "Cell cycle stage-dependent induction of $G_2$ phase arrest by different antitumor agents." *Eur. J. Cancer* 14:741–745 (1978); Soreson C. M. et al., "Influence of cis-diamminedichloroplatinum(II)-induced cytotoxicity: role of $G_2$ arrest and DNA double-strand breaks," *Cancer Res.* 48:4484–4488 (1988)). The $G_2$ arrest can permit repair of DNA and ensures that DNA replication is complete before the cell enters into mitosis. Based on such findings it has been proposed and it is now largely accepted that the main function of normal p53 is to preserve genomic integrity by acting as the "guardian of the genome" (Lane, D. P., "p53, guardian of the genome," *Nature* (Lond.) 358:15–16 (1992)). As a consequence, tumor cells with no or mutated p53 function lose their sensitivity to a wide variety of DNA-damaging agent (Fan S. et al., "p53 gene mutations are associated with decreased sensitivity of human lymphoma cells to DNA damaging agents." *Cancer Res.* 54:5824–5830 (1994)); Lee J. M. et al., "p53 mutations increase resistance to ionizing radiation," *Proc. Natl. Acad. Sci. USA* 90:5742–5746 (1993); and Lowe S. W. et al., "p53 status and the efficacy of cancer therapy in vivo." *Science* (Washington D.C.) 266:807–810 (1994)). It is possible that this observation occurs because p53 stimulates a more efficient DNA repair process. Therefore, treatment of tumor cells deficient in p53 normal function with topoisomerase inhibitors alone is unlikely to be curative, since $G_2$ arrest induced by the use of low doses would allow DNA repair to occur prior to mitosis, thus preventing potentially lethal lesions from killing tumor cells, while S phase arrest induced with the use of high doses may inflict high levels of DNA damage on the normal cells. One way to increase the sensitivity of these tumor cells to DNA damaging agents is to modulate events at checkpoints in the S and $G_2$ phases to which only damaged tumor cells with mutant p53 would progress. At the same time, normal cells that pass the $G_1$ checkpoint during this modulation would also progress to $G_2$ and would also be sensitive to modulation at S and $G_2$ checkpoints. However, the wild-type p53 seems to protect these cells from abrogation at these checkpoints (Russell, K. J. et al., "Abrogation of the $G_2$ checkpoint results in differential radiosensitization of $G_1$ checkpoint-deficient and competent cells," *Cancer Res.* 55:1639–1642 (1995); and Powell, S. N. et al., "Differential sensitivity of p53– and p53+ cells to caffeine-induced radiosensitization and override of $G_2$ delay," *Cancer Res.* 55:1643–1648 (1995)).

A variety of agents such as caffeine and other methylxanthines can override the DNA damage-dependent $G_2$-checkpoint and enhance drug-induced cytotoxicity (Russell K. J. et al., "Abrogation of the $G_2$ checkpoint results in differential radiosensitization of $G_1$ checkpoint-deficient and competent cells," *Cancer Res.* 55:1639–1642 (1995); and Fan S. et al., "Disruption of p53 function sensitizes breast cancer MCF-7 cells to cisplatin and pentoxifylline," *Cancer Res.* 55:1649–1654 (1995)). However, plasma drug concentrations higher than the maximum tolerated doses are required to achieve this effect in clinical settings. In search of new $G_2$-checkpoint inhibitors, a staurosporine analog, 7-hydroxystaurosporine (UCN-01), has been found to abrogate the cisplatin-induced S and $G_2$ checkpoints and to enhance its cytotoxicity in CHO and HT-29 cells lacking normal p53 function (Bunch R. T. et al., "Enhancement of cisplatin-induced cytotoxicity by 7-hydroxystaurosporine (UCN-01), a new $G_2$-checkpoint inhibitor," *Clinical Cancer Res.* 2:791–797 (1996); and Wang Q. et al., "UCN-01: a potent abrogator of $G_2$ checkpoint function in cancer cells with disrupted p53." *JNCI* 88:956–965 (1996)).

SUMMARY OF THE INVENTION

It has now been discovered that staurosporines, such as UCN-01 (7-hydroxystaurosporine), have the ability to abrogate the topoisomerase I inhibitor-induced (such as CPT-induced) S phase arrest and to enhance CPT-induced cytotoxicity in human breast cancer cells lacking normal p53 function compared to normal cells with wild-type p53. This discovery suggests that: a) staurosporines inhibit, topoisomerase-induced S phase arrest in tumor cells defective in p53 function and enhance topoisomerase-induced cytotoxicity in a synergistic manner, b) normal cells with normal p53 function are protected from topoisomerase I-induced damage by arresting in the $G_0/G_1$ phase, and c) the abrogation of S phase arrest occurs with the use of sublethal doses of staurosporines. Thus, in one aspect of the present invention, a staurosporine, such as UCN-01, is used in combination chemotherapy with topoisomerase inhibitor-based regimens to improve the therapeutic use and clinical application of these agents against breast cancer.

The cytotoxicity of camptothecin (CPT) is correlated with cell cycle response in normal and tumor cells. Low doses of CPT arrest cells in the $G_2/M$ phase and inhibit DNA synthesis, however, higher doses cause arrest of cells in S phase. Thus modulation of events at S and $G_2$ checkpoints provides an opportunity to enhance CPT-induced cytotoxicity in tumor cells. UCN-01, a specific inhibitor of protein kinase C (PKC), abrogates CPT-induced activation of S and $G_2$ checkpoints in human MDA-231 and GI 101A breast carcinoma cells; both are mutants for p53 gene. This abrogation occurs with the use of sublethal doses (100 nM) of UCN-01 and correlates with the enhancement of CPT-induced cytotoxicity. Using the MTT assay and analyzing the data using the median-effect principle, synergistic cytotoxic interactions have been shown to exist between the topoisomerase inhibitor, such as CPT, and the staurosporine analog, such as UCN-01, against these tumor cells. In normal cells, however, abrogation of the S phase arrest causes accumulation in $G_0/G_1$ phase, perhaps by the presence of wild-type p53 activity, with no change in the topoisomerase I inhibitor-induced cytotoxicity. The results indicate that the staurosporine is enhancing the progression of tumor cells through S phase and thus greatly increasing topoisomerase I inhibitor-induced cytotoxicity. Normal cells, however, are able to arrest in $G_0/G_1$ and thus avoid increased toxicity induced by CPT. These findings confirm usefulness of combining a staurosporine, such as UCN-01, in topoisomerase I inhibitor-based drug therapy for the treatment of breast cancer.

BRIEF DESCRIPTION OF THE DRAWINGS

Figure 7A:
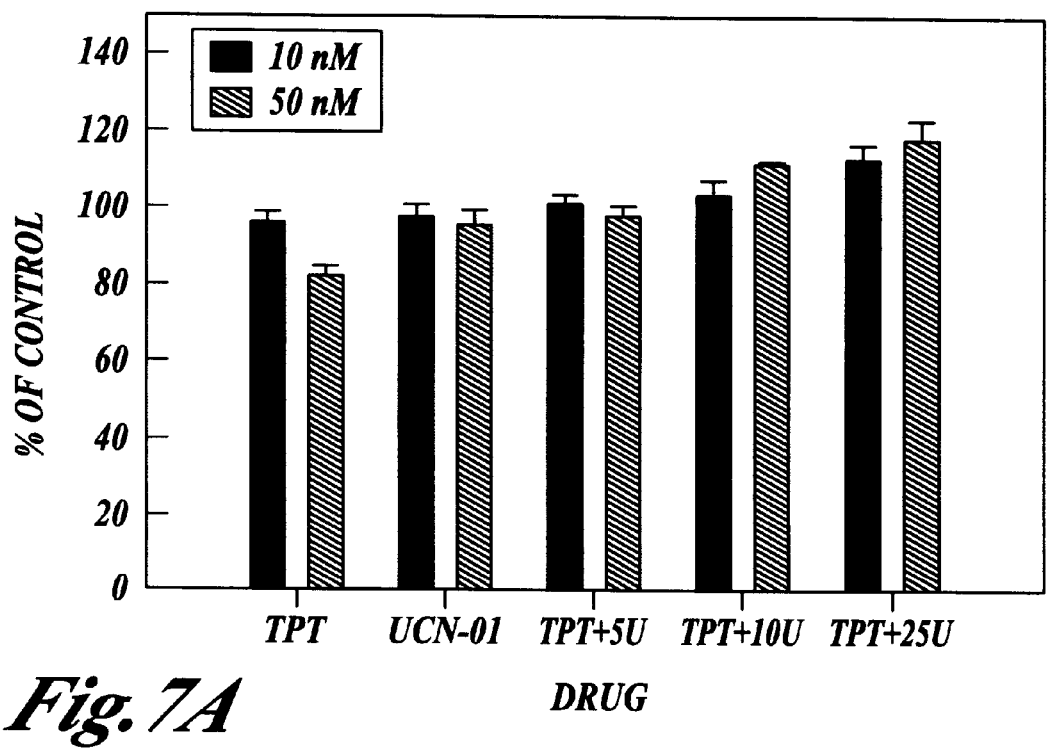
Figure 7B:
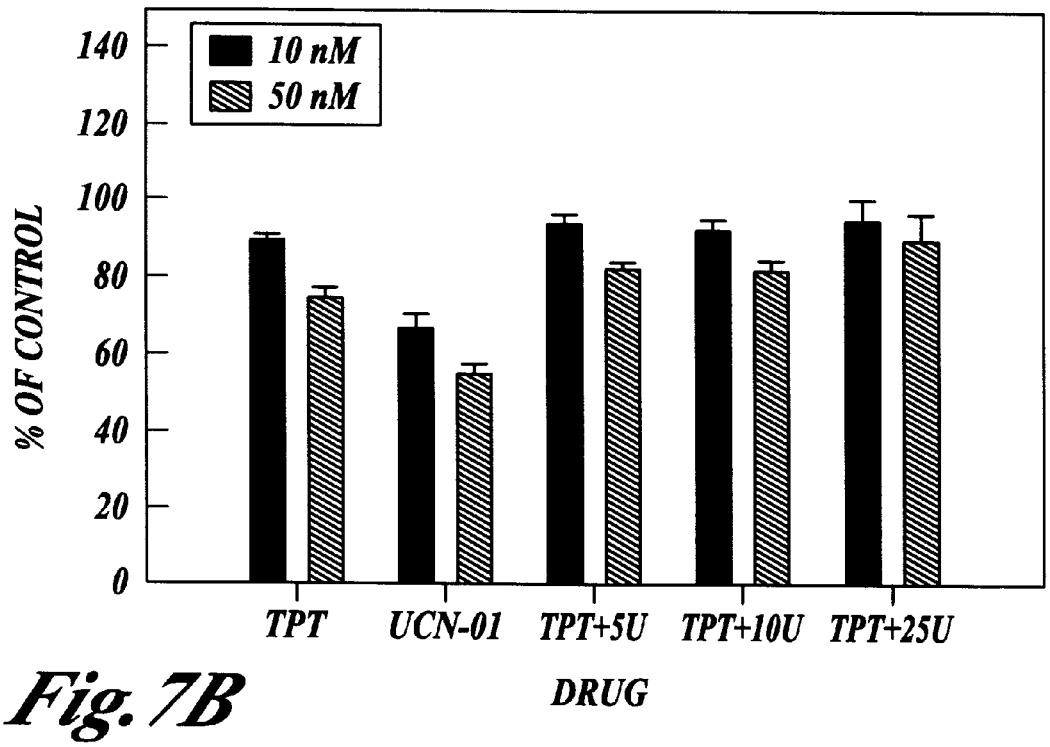

The foregoing aspects and many of the attendant advantages of this invention will become more readily appreciated as the same becomes better understood by reference to the following detailed description, when taken in conjunction with the accompanying drawings, wherein:

FIG. 1 shows the chemical structures of UCN-01 (7-hydroxystaurosporine), staurosporine and camptothecin;

FIGS. 2A–2C show the dose-response curves for the exposure of GI 101A (FIG. 2A), MDA-231 (FIG. 2B) and endothelial cells (FIG. 2C) to combinations of CPT and sublethal doses of UCN-01, as described in Example 1. Cells were exposed with various doses of CPT (□), UCN-01 (○) and 100 nM UCN-01+CPT (■) for 24 h. Following drug treatment, the cells were reincubated in drug-free medium, and the surviving cell fraction was determined by the MTT assay. Points represent the means of quadruplicate determinations±SE, obtained in 2–3 independent experiments;

FIGS. 3A and 3B show the combined effect of 24 h exposure of GI 101A (▲) and MDA-231 (△) cells to CPT plus UCN-01, as described in Example 2. Computer-generated curves describe the combined effects of CPT:UCN-01 at fixed dose ratios of 1:1 for 24 h. Results are plotted as a function of the fraction of treated cells affected following cytotoxicity assays (FIG. 3A) or [$^3$H]thymidine incorporation assays (FIG. 3B) versus the combination index (fa-CI plot) under a mutually nonexclusive assumption. All points lying above a combination index (CI) of 1 are antagonistic, those lying below a CI of 1 are synergistic, and those lying at a CI of 1 are additive. Interactions of CPT and UCN-01 are strongly synergistic in both cell lines when analyzed for growth inhibition, while antagonistic when analyzed for DNA synthesis;

FIG. 7 shows DNA synthesis in TPT and UCN-01 treated MDA-231 cells (p53 mut) (FIG. 7A) and HMEC/E6 (p53 inactive) (FIG. 7B) as measured by BrdU incorporation assay, as described in Example 5. The data show antagonistic effects of TPT-induced inhibition of DNA synthesis in the presence of UCN-01, thus the interaction is antagonistic with respect too DNA synthesis. Mean±SE of eight determinations.

FIG. 8 shows the influence of UCN-01 on abrogation of S phase arrest in MDA-231 cells, as described in Example 6. Cells were incubated with the indicated concentrations of TPT (FIG. 8A), UCN-01 (FIG. 8B) and combination of TPT+25 nM UCN-01 (FIG. 8C) for 24 h. Cells were fixed, stained with PI and analyzed by FACS for cell cycle phase progression.

Figure 9A:
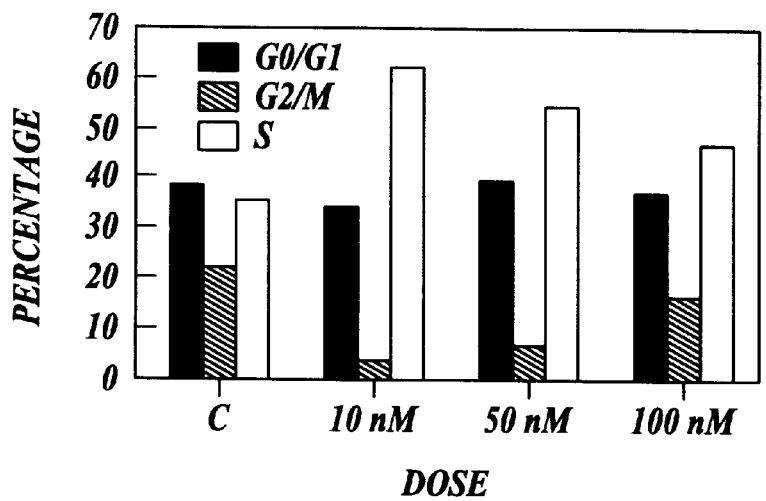
Figure 9B:
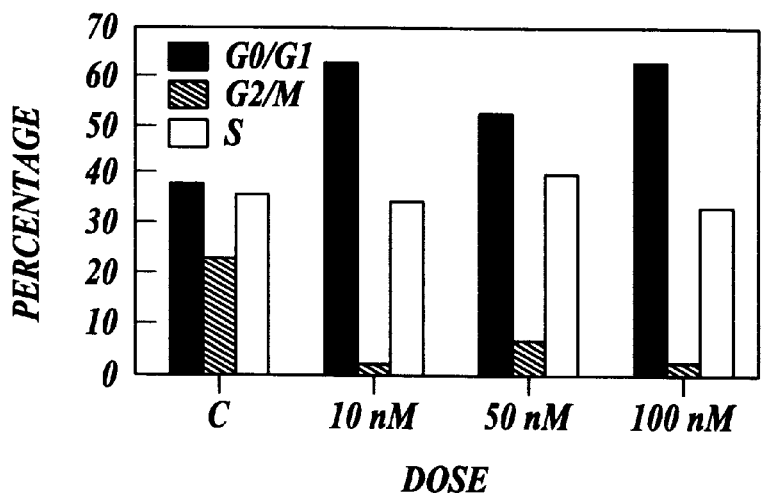
Figure 9C:
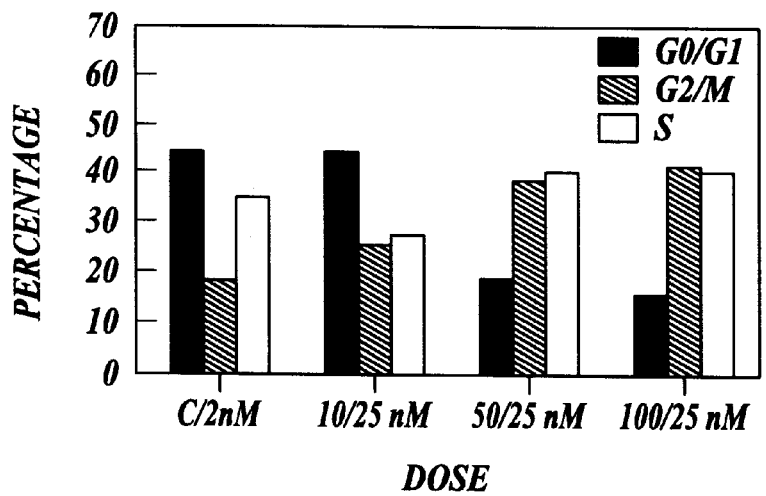

FIGS. 9A–9C show the percentage of cell population in G, S, and G/M phases in response to drug treatment, as described in Example 6. TPT-damaged MDA-231 cells showed a reduction in the percentage of cells arrested in S phase in the presence of 25 nM UCN-01.

Figure 10A:
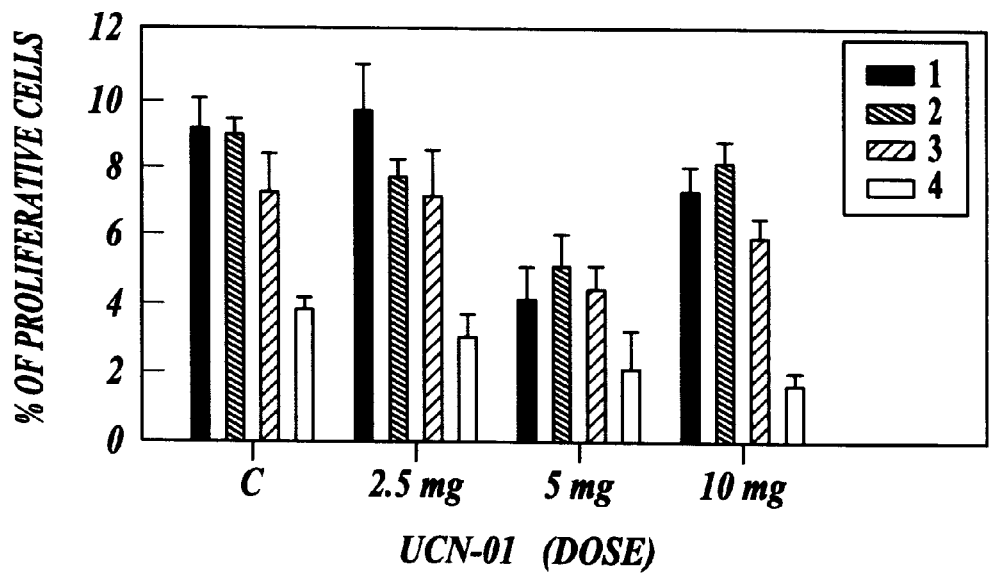
Figure 10B:
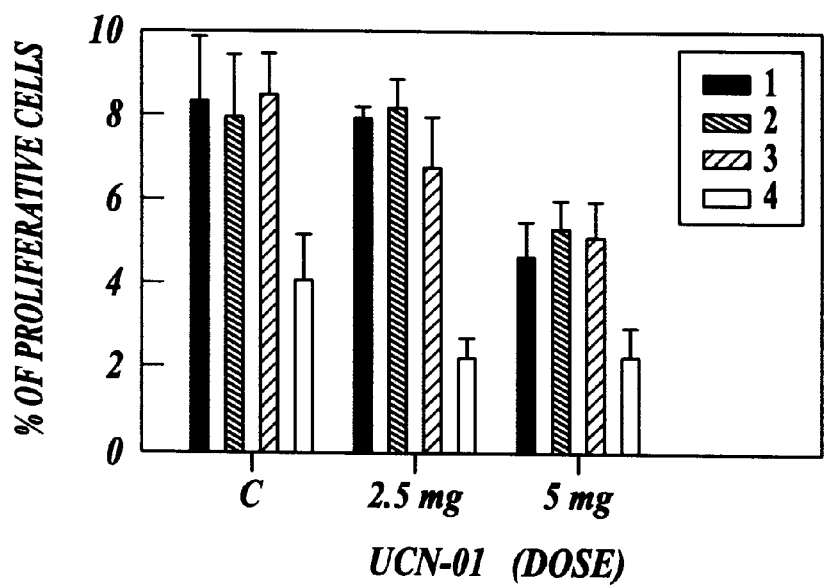

FIGS. 10A and 10B show the dose-dependent inhibition of hyperproliferative epithelial cells of C57/BL mouse small intestine with UCN-01, as described in Example 7. Analysis of images from duodenum, 1; jejunum, 2; ileum, 3; and colon, 4 stained for BrdU following 3 h treatment (FIG. 10A) and 24 h treatment (FIG. 10B). Results are expressed as proliferative cells (%) recognized by image analysis based on black and white areas (five) as described above. Mean±SE of six experiments. That data show that the use of 5 mg/kg UCN 01 caused a significant suppression of hyperproliferative cells as compared to control.

FIGS. 11A, 11B and 11C shows flow cytometric dual parameter dot plots of BrdU labeling vs. DNA content in murine bone marrow cells following 3 hr treatment with UCN-01, as described in Example 7. The cells were pulsed with BrdU for 3 hr, stained with anti-BrdU antibody and with PI. A. control (−ve) untreated cells without BrdU-antibody, (+ve) untreated control+BrdU antibody+PI.

Figure 11D:
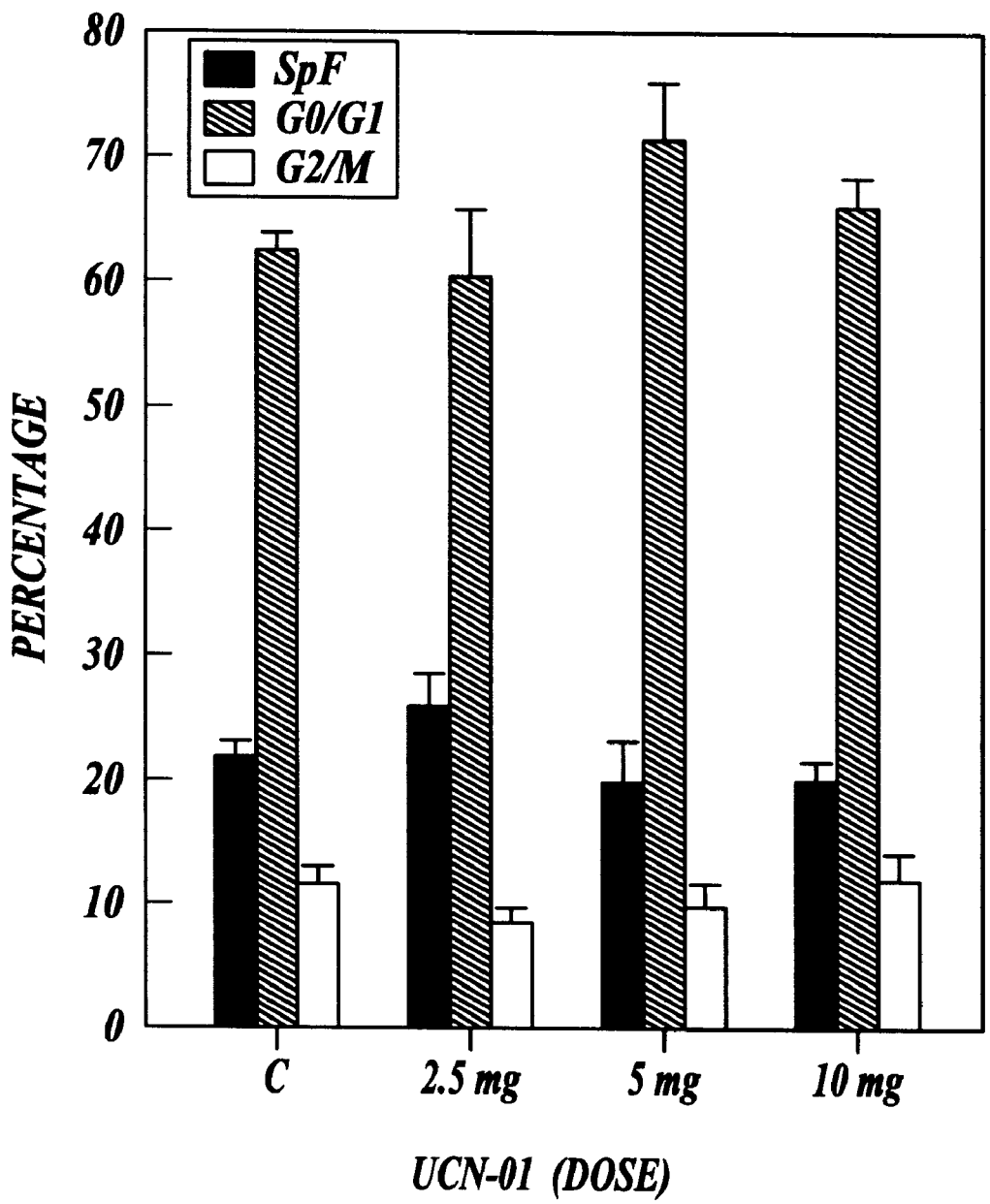

FIG. 11D shows the percentage of $G_1$ and S phase arrested cells following treatment with UCN-01. These values were used to determine the $G_1$/S arrest by dividing $G_1$:S ratio (treated) by $G_1$:S (untreated).

Figure 12A:
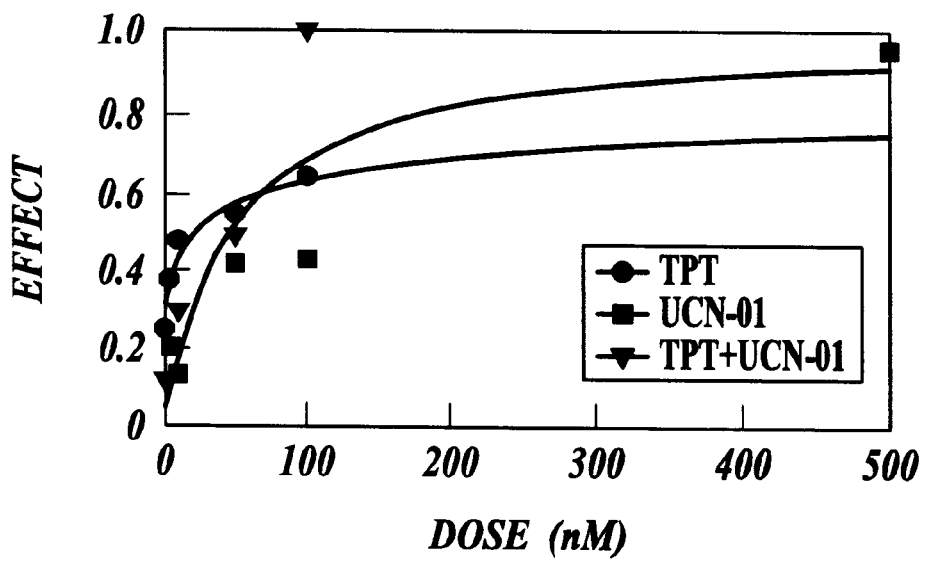
Figure 12B:
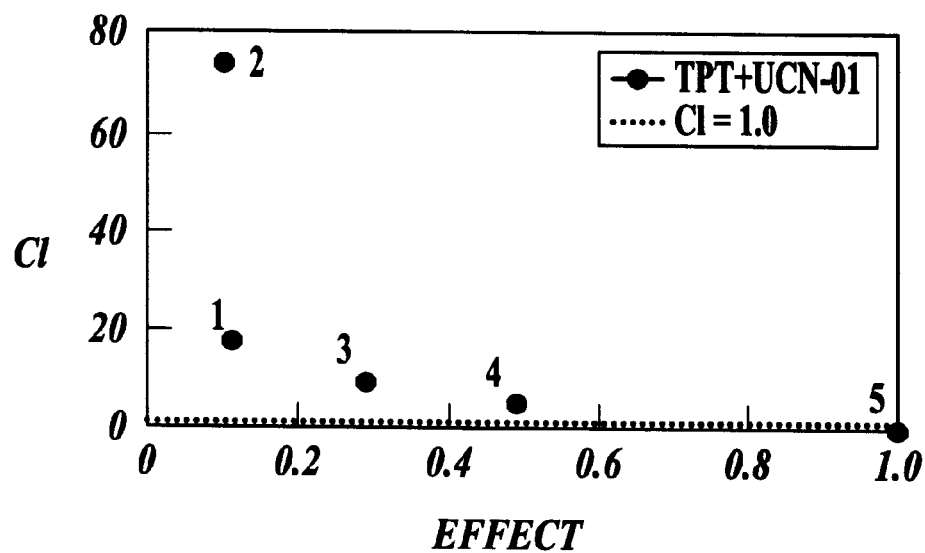

FIGS. 12A and 12B show the synergyanalysis of the interaction between TPT and UCN-01 on murine bone marrow cells, as described in Example 8. The values are the means of two independent experiments. In FIG. 12B, CI>1, antagonism; CI<1, synergism; CI=1, additive. Note that all points are above CI+1, thus antagonistic interaction was obtained.

Figure 13:
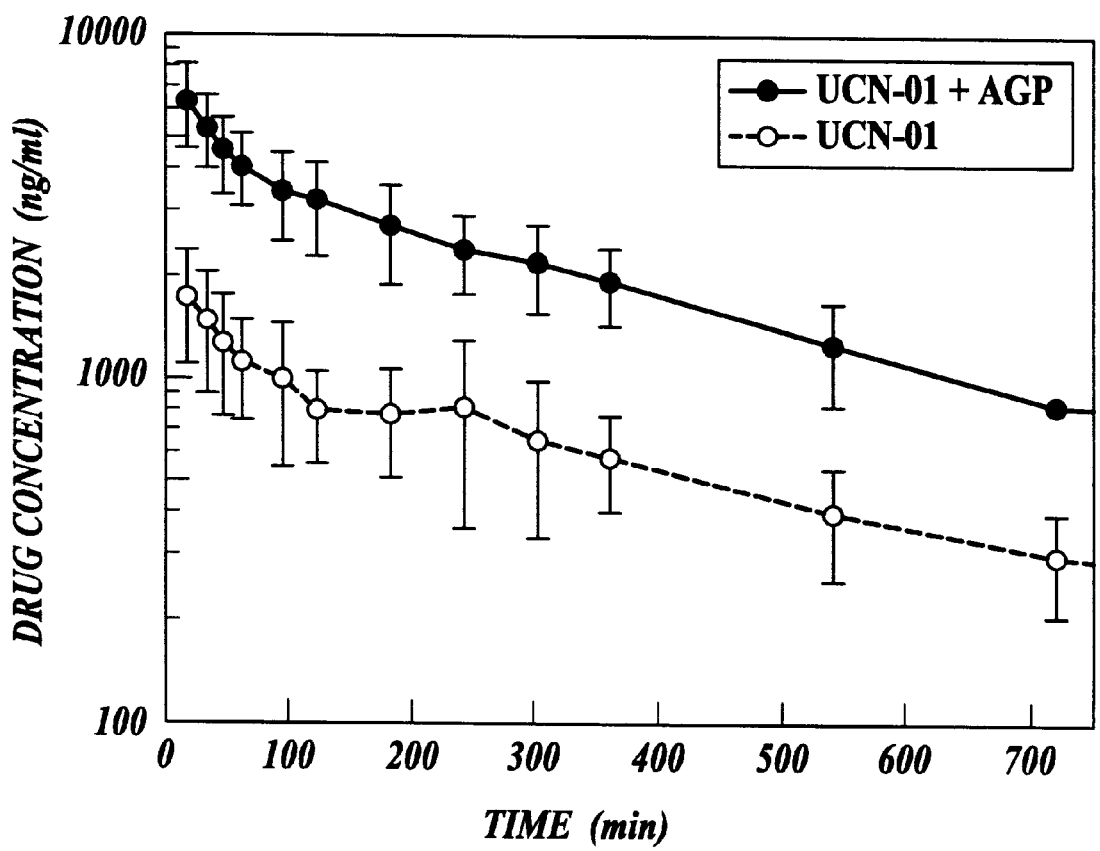

FIG. 13 shows the plasma-concentration profile of UCN-01 in healthy Wistar male rats, as described in Example 9. Plasma samples were determined following i. v. administration of 10 mg/kg UCN-01 (◯) or 10 mg/kg UCN-01+10 mg AGP (●). Mean±SD of five different experiments.

Figure 14A:
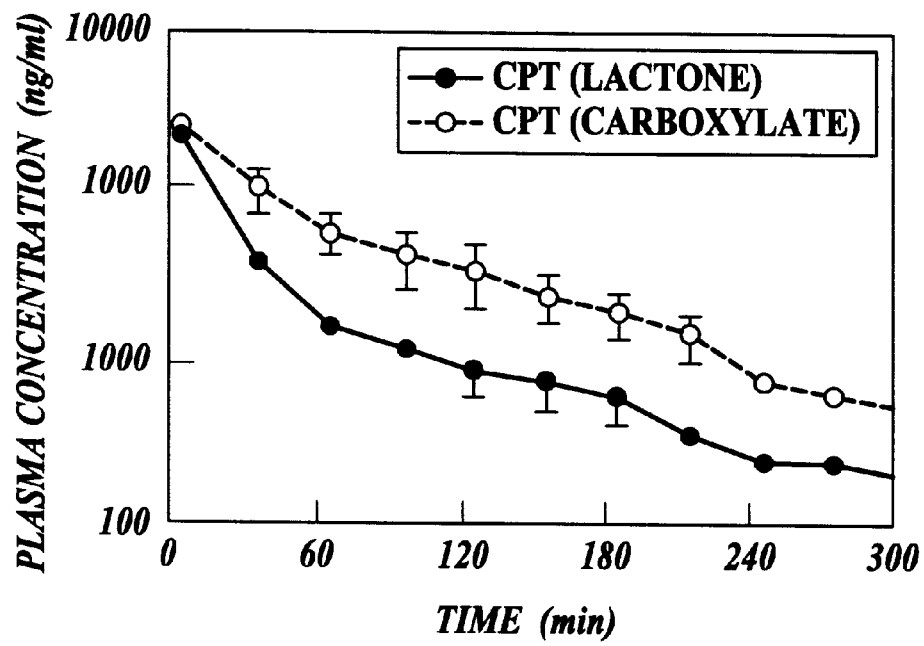
Figure 14B:
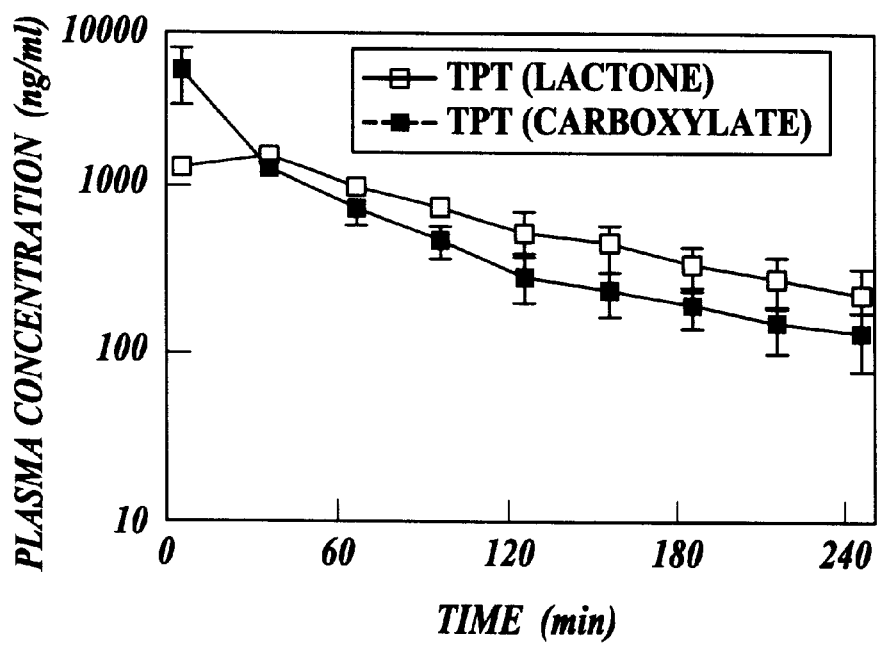

FIGS. 14A and 14B show the plasma concentration-time profiles of CPT (FIG. 14B) and TPT (FIG. 14A) in rats, as described in Example 11. The plasma elimination declined biexponentially, and the drugs were distributed to all tissues then eliminated with half life of 85 min, and 92 min for CPT and TPT, respectively.

DETAILED DESCRIPTION OF THE PREFERRED EMBODIMENT

In one aspect, the present invention relates to pharmaceutical compositions comprising a topoisomerase I (topo I) inhibitor, such as camptothecin or a camptothecin analog, and a staurosporine such as 7-hydroxystaurosporine, together with a pharmaceutically acceptable carrier or diluent. In other aspects, the present invention relates to methods of inhibiting the growth of cancer cells which comprises contacting the cells with an effective cancer cell growth inhibiting amount of a pharmaceutical composition of the invention. In yet other aspects, the present invention relates to methods of enhancing topoisomerase I inhibitor concentrations in tumor cells and/or inhibiting the growth of tumor cells in a mammalian species afflicted therewith which comprises administering to such mammal an effective tumor cell growth inhibiting amount of a pharmaceutical composition of the invention to obtain inhibition of growth of the tumor cells while protecting normal cells from topoisomerase I inhibitor induced cytotoxicity.

Topoisomerase I inhibitors useful in the practice of the invention include camptothecin and camptothecin analogs. By the term "camptothecin" or "a camptothecin analog" is meant any tumor cell growth inhibiting compound which is structurally related to camptothecin. Camptothecin or camptothecin analogs useful in the practice of the invention include, but are not limited to, topotecan, irinotecan and 9-aminocamptothecin. Such compounds also include, but are not limited to, any tumor cell growth inhibiting camptothecin analog claimed or described in U.S. Pat. No. 5,004,758, U.S. Pat. No. 4,604,463, U.S. Pat. No. 4,473,692, U.S. Pat. No. 4,545,880, European Patent Application Publication No. EP 0 088 642, U.S. Pat. No. 4,342,776, European Patent Application Publication No. EP 418 099, U.S. Pat. No. 4,513,138, and U.S. Pat. No. 4,399,276, the entire disclosure of each of which is hereby incorporated by reference.

When a camptothecin analog is employed in the practice of the invention, the camptothecin analog is preferably selected from the group consisting of topotecan, irinotecan and 9-aminocamptothecin. Preferably the camptothecin analog is water soluble. Topotecan is a presently preferred camptothecin analog for use in the practice of the present invention. By the term "topotecan" as used herein is meant (S)-9-dimethylaminomethyl-10-hydroxycamptothecin and any pharmaceutically acceptable salt, hydrate or solvate thereof. Topotecan's chemical name is (S)-10 [(dimethylamino)methyl]-4-ethyl-4,9-dihydroxy-IH-pyrano [3',4':6,7]ind olizino[1,2-b]quinolone-3,14(4H,12H)-dione. Topotecan is water-soluble by virtue of the presence of the basic side-chain at position 9 which forms salts with acids. Preferred salt forms of topotecan include the hydrochloride salt, acetate salt and methanesulfonic acid salt. An alkali metal salt form of the carboxylate formed on alkaline hydrolysis of the E-ring lactone of topotecan would also yield a soluble salt, such as the sodium salt. The preparation of topotecan (including pharmaceutically acceptable salts, hydrates and solvates thereof) as well as the preparation of oral and parenteral pharmaceutical compositions comprising topotecan and an inert, pharmaceutically acceptable carrier or diluent, is extensively described in U.S. Pat. No. 5,004, 758, issued on Apr. 2, 1991 and European Patent Application No. 88311366.4, published on Jun. 21, 1989 as Publication No. EP 0 321 122.

As use herein, the term "staurosporine" is intended to include 7-hydroxystaurosporine (also referred to as UCN-01 as disclosed in U.S. Pat. No. 4,935,415, the disclosure of which is incorporated hereby by this reference) as well as staurosporine derivatives having the biological effects of 7-hydroxystaurosporine for purposes of this invention.

In one aspect, this invention relates to methods of inhibiting the growth of tumor cells in a human afflicted therewith which comprises administering to such human an effective tumor cell growth inhibiting amount of a topoisomerase I inhibitor, preferably camptothecin or a camptothecin analog, and a substituted or unsubstituted staurosporine compound. One preferred aspect of this invention relates to a method of inhibiting the growth of tumor cells in a human afflicted therewith which comprises administering to such human an effective tumor cell growth inhibiting amount of topotecan and 7-hydroxystaurosporine to obtain inhibition of the growth of tumor cells in the human while protecting normal cells from topoisomerase I inhibitor induced cytotoxicity.

By the term "inhibiting the growth of cancer cells" or "inhibiting the growth of tumor cells" as used herein is meant the inhibition of the growth of cancer or tumor cells which are sensitive to the method of the subject invention, i.e., therapy involving the administration of an effective amount of the combination of a topoisomerase I inhibitor, such as topotecan, and a substituted or unsubstituted staurosporine compound, such as 7-hydroxystaurosporine, to a human or other mammalian subject afflicted therewith. Preferably such treatment also leads to the regression of tumor growth, i.e., a decease in size of a measurable tumor. Most preferably, such treatment leads to the complete regression of the tumor. In the practice of the invention, inhibition of the growth of tumor cells is obtained while protecting normal cells from damage commonly associated with topoisomerase I induced cytotoxicity.

By the term "administering" or "administered" as used herein is meant parenteral and/or oral administration. By "parenteral" is meant intravenous, subcutaneous or intramuscular administration. In the methods of the subject invention, the camptothecin or camptothecin analog may be administered simultaneously with the staurosporine compound, or the compounds may be administered sequentially, in either order. It will be appreciated that the actual preferred method and order of administration will vary according to, inter alia, the particular formulation of the camptothecin or camptothecin analog (such as topotecan) being utilized, the particular formulation of the staurosporine compound (such as 7-hydroxystaurosporine) being utilized, the particular tumor cells being treated, and the particular host being treated. The optimal method and order of administration of the compounds of the invention for a given set of conditions can be ascertained by those skilled in the art using conventional techniques and in view of the information set out herein.

By the term "effective tumor cell growth inhibiting amount" of the compounds of the invention as used herein is meant a course of therapy which will result in inhibiting the growth of tumor cells sensitive to such therapy in a human afflicted therewith. Preferably, such course of therapy will result in the administration of a lower dose of the compounds of the invention than is required when such compound is administered as the sole chemotherapeutic agent; and/or will result in enhancement of the tumor cell growth inhibiting efficacy of the compounds of the invention as compared to when such compound is administered as the sole chemotherapeutic agent. It will be appreciated that the actual preferred course of therapy will vary according to, inter alia, the mode of administration of the compounds, the particular formulation of the topoisomerase I inhibitor compound (such as topotecan) being utilized, the particular formulation of the staurosporine compound (such as 7-hydroxystaurosporine) being utilized, the mode of administration, the compounds, the particular tumor cells being treated and the particular host being treated. The optimal course of therapy for a given set of conditions can be ascertained by those skilled in the art using conventional course of therapy determination tests and in view of the information set out herein.

In the methods of the subject invention, for parenteral administration of a camptothecin or camptothecin analog, the course of therapy generally employed is from about 0.1 to about 300.0 mg/m$^2$ of body surface area per day for about one to about five consecutive days. More preferably, the course of therapy employed is from about 0.1 to about 100 mg/m$^2$ of body surface area per day for about five consecutive days. Most preferably, the course of therapy employed for topotecan is from about 1.0 to about 2.0 mg/m$^2$ of body surface area per day for about five consecutive days. Preferably, the course of therapy is repeated at least once at about a seven day to about a twenty-eight day interval (from the date of initiation of therapy) depending upon the initial dosing schedule and the patient's recovery of normal tissues. Most preferably, the course of therapy continues to be repeated based on tumor response. Preferably, the parenteral administration of a camptothecin or camptothecin analog will be by short (e.g., 30 minute) or prolonged (e.g., 24 hour) intravenous infusion. More preferably, the compound will be administered by a 30 minute intravenous infusion.

In the methods of the subject invention, for oral administration of a carnptothecin or camptothecin analog, the course of therapy generally employed is from about 1.0 to about 500.0 mg/m$^2$ of body surface area per day for about one to five consecutive days. More preferably, the course of therapy employed for topotecan is from about 1.5 to about 5.0 mg/m$^2$ of body surface area per day for about five consecutive days. Preferably, the course of therapy is repeated at least once at about a seven day to about a twenty-eight day interval (from the date of initiation of therapy) depending upon the initial dosing schedule and the patient's recovery of normal tissues. Most preferably, the course of therapy continues to be repeated based on tumor response.

In the methods of the invention, for parenteral administration of a staurosporine, such as 7-hydroxystaurosporine, effective amounts of the staurosporine to be administered will generally range from about 0.5 to about 15 mg/m$_2$ of body surface area per day, more preferably from about 0.5 to about 15 mg/m$_2$ of body surface area per day, and most preferably from about 0.5 to about 1.5 mg/m$^2$ of body surface area per day.

The pharmaceutical compositions of the invention contains both a camptothecin or camptothecin analog and a substituted or unsubstituted staurosporine compound, as well as a pharmaceutically acceptable carrier excipient or diluent. Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Pharmaceutical compositions containing the topoisomerase I inhibitor and staurosporine compounds of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof. Preferably, such pharmaceutical composition is in the form of a freeze-dried mixture of the two active ingredients in a unit dosage form, prepared by conventional techniques, which can be reconstituted with water or other suitable infusion liquid at the time of administration.

It will be recognized by one of skill in the art that the content of the active ingredients in the pharmaceutical composition of this invention may vary quite widely depending upon numerous factors, such as, the desired dosage and the pharmaceutically acceptable carrier being employed. For administration, in the pharmaceutical composition of the invention, the content of the camptothecin or camptothecin analog will usually be 10:1 to 1000:1 by weight, with respect to the content of the substituted or unsubstituted staurosporine compound present in the composition. Preferably, the pharmaceutical composition of the invention will contain from 5 mg to 500 mg of the substituted or unsubstituted staurosporine compound, and from 100 mg to 10,000 mg of the camptothecin or camptothecin analog. Physiological pH of injectables or infusion drug combinations will be established by inclusion of buffering agents as is known in the pharmaceutical formulation art.

These and other aspects of the invention may become more readily apparent in connection with the following representative examples which are presented for purposes of illustration and not by way of limitation.

EXAMPLE 1

Enhancement of CPT-Induced Cytotoxicity by UCN-01 in Tumor Cells

The response of MDA-231 and GI 101A tumor cells to CPT and the effect of UCN-01 on the sensitivity of these cells for 24 h drug exposure as compared to normal endothelial cells (BVEC) is illustrated in FIGS. 2A–2C. In the presence of CPT alone, GI 101A and MDA 231 cells (FIGS. 2A and 2B, respectively) were inhibited 50% by 300 nM and 200 nM CPT, while growth of normal endothelial cells (FIG. 2C) was inhibited by 50% at doses >1 mM CPT. Sublethal doses of UCN-01 (100 nM) shifted the CPT dose-response curves in tumor cells to the left, with minimal effect on normal endothelial cells. As seen in FIGS. 2A and 2B, UCN-01 greatly enhanced CPT cytotoxicity in GI 101A and MDA 231 cells (about 30- to 40-fold, respectively) when 100 nM doses were present for 24 h, as compared to the absence of UCN-01. For BVEC (FIG. 2C), sublethal doses of UCN-01 produced minimal leftward shift in the dose-response curves to CPT.

Materials and Methods

Cell lines and Culture. The two human breast carcinoma cell lines with mutant p53, MDA-231 and GI 101A were maintained as monolayer cultures in RPMI-1649 medium (Gibco, Grand Island, N.Y.) supplemented with 10% bovine calf serum (Hyclone, Logan, Utah) at 37° C. in a humidified 5% $CO_2$ atmosphere. Normal bovine venular endothelial cells (BVEC) were maintained in DMEM media (Gibco) supplemented with 1 mM sodium pyrovate (Gibco), and 20% bovine calf serum (Hyclone). Cell viability was determined using the trypan blue exclusion test. To ensure an exponential growth, cells were plated in fresh medium 24 h before each treatment.

Drugs and Chemical Reagents. CPT (NSC 94600) and UCN-01 (NSC 638850) were obtained from the Drug Development Branch, National Cancer Institute, NIH (Bethesda, Md.) dissolved in dimethyl sulfoxide (DMSO) at 4 mM and 1 mM, respectively, aliqoted and stored at −70° C. Further dilutions were made in culture medium just before use. The final concentration of DMSO in culture did not exceed 0.1% (v/v) which is non toxic to cells. Thiazoyl blue (MTT) was purchased from Sigma Chemical Co. (St. Louis, Mo.), [methyl-$^3$H]thymidine (7 Ci/mmol) was obtained from Andotek (Irvine, Calif.). All other chemicals were reagent grade.

Drug Treatment and Survival Curves. Cytotoxicity studies were initiated by plating $2 \times 10^4$ cells obtained from exponentially growing cultures in 24-well tissue culture plates (Coming-Costar, Cambridge Mass.) in the appropriate medium. Following 24 h incubation at 37° C., drugs were added to quadruplicate wells and incubated for 24 h, the wells were washed twice with prewarmed phosphate-buffered saline (PBS) and then incubated with drug-free medium for 2–3 doubling times.

Cell survival was determined using a semiautomated tetrazolium (MTT)-based calorimetric assay, as described, Daoud S S and Juliano R L. "Modulation of doxorubicin resistance by valinomycin (NSC 122023) and liposomal valinomycin in Chinese hamster ovary cells." *Cancer Res.* 49:2661–2667 (1989); and Daoud S S and Forde N H. "Synergistic cytotoxic actions of cisplatin and liposomal valinomycin on human ovarian carcinoma cells." *Cancer Chemother. Pharmacol.* 28:370–376 (1991). The effect of UCN-01 on CPT-induced cytotoxicity was evaluated by exposing cells to graded concentrations of the latter drug in the presence and absence of subtoxic doses of UCN-01. The concentration of drugs causing 50% inhibition of cell growth ($IC_{50}$) for the drug combination was calculated by logarithmic analysis.

Drug Combinations and Data Analysis. Cells were exposed to UCN-01 and CPT either alone or in combination at fixed dose ratios for 24 h. The surviving cell fraction was determined using the MTT assay (cytotoxicity effects) as described above or $^3$H-thymidine incorporation assay (antiproliferative effects) as described, Jones C B, Clements M K, Wasi S and Daoud S S. "Sensitivity to camptothecin of human breast cancer cells and normal bovine endothelial cells, in vitro." *Cancer Chemother. Pharmacol.* (in press, 1997). Synergy of activity was analyzed according to the median-effect principle, Chou T-C and Talalay P. "Quantitative analysis of dose-effect relationships: The combined effects of multiple drugs or enzyme inhibitors." *Adv. Enzyme Regul.* 22:27–55 (1984) and plotted as combination index (CI) versus fraction affected (Fa) as described in Chou T-C and Talalay P. "Quantitative analysis of dose-effect relationships: The combined effects of multiple drugs or enzyme inhibitors." *Adv. Enzyme Regul.* 22:27–55 (1984). A CI of 1 at the 50% growth inhibition ($IC_{50}$ value) indicates an additive interaction, a CI>1 indicates antagonism and a CI<1 indicates synergism.

Cell Cycle Analysis. Flow cytometric analysis of the cell cycle was performed as described in Jones C B, Clements M K, Wasi S and Daoud S S. "Sensitivity to camptothecin of human breast cancer cells and normal bovine endothelial cells, in vitro." *Cancer Chemother. Pharmacol.* (in press, 1997).

Briefly, cells treated with 100 nm CPT, 100 nM UCN-01 or drug combination were scraped into ice-cold PBS. Cell suspensions were centrifuged (1000 rpm for 10 min) and then washed twice with PBS. After the final wash, cell pellets were resuspended in 1 ml PBS buffer and fixed with 70% (v/v) ethanol at 4° C. overnight. DNA was then stained by incubating cells in 0.1% triton X-PBS buffer containing 50 mg/ml propidium iodide and 100 mg/ml RNase A overnight at 4° C. DNA content was determined on a Becton Dickinson FACScan flow cytometer. Propidium iodide-stained nuclei were excited with a 488-nm air cooled argon laser, and fluorescence emission greater than 680 nm was recorded on a linear scale and cell cycle distribution was quantitated by gating control cells and maintaining gates for treated cells using doublet discrimination module.

EXAMPLE 2

Synergy between UCN-01 and CPT in Tumor Cells

To determine whether the interaction between UCN-01 and CPT was truly synergistic, tumor cells in culture were exposed to UCN-01 and CPT either alone or in combination over a wide range of doses but at a fixed dose ratio for 24 h. In these experiments (CPT:UCN-01 molar ratio 1:1), the median-effect doses, Dm, for CPT were 104 nM and 28 nM in GI 101A and MDA 231, respectively. Computed regression coefficients for the linearized dose-effect curves were >0.9, indicating that the data fulfilled the criteria for computation for the combination index (CI) according to Chou T-C et al., "Quantitative analysis of dose-effect relationships: The combined effects of multiple drugs or enzyme inhibitors," *Adv. Enzyme Regul.* 22:27–55 (1984). The composite fa-CI plot for such experiments is presented in FIG. 3A. Analysis of the data for these experiments suggested that the two drugs acted synergistically over the majority of concentrations tested. The data were analyzed under mutually nonexclusive conditions, since it was assumed that the two drugs act toward different targets; however, similar results were obtained when data were analyzed under mutually exclusive conditions.

When the antiproliferative activity of the drug combination was determined by [$^3$H]-thymidine incorporation assay, antagonistic effect was observed (FIG. 3B). In these experiments, cells were treated with the each drug alone and in combination (CPT:UCN-01 molar ratio 1:10) and the DNA synthesis was determined following incubation for 4 h with [$^3$H]-thymidine. Analysis of the data of such experiments (FIG. 3C), showed that the two drugs acted antagonistically over the majority of concentrations tested (25%–100%). Thus the results of the above experiments demonstrate that UCN-01 enhanced CPT-induced cytotoxicity (growth inhibition) in tumor cells that lack p53 function with minimal effects on normal endothelial cells. The antiproliferative activity (DNA synthesis) of CPT on tumor cells was inhibited in the presence of UCN-01.

EXAMPLE 3

Abrogation of CPT-Induced S/$G_2$ Activation with UCN-01 in Tumor Cells

Figures 4A, 4B, 4C:
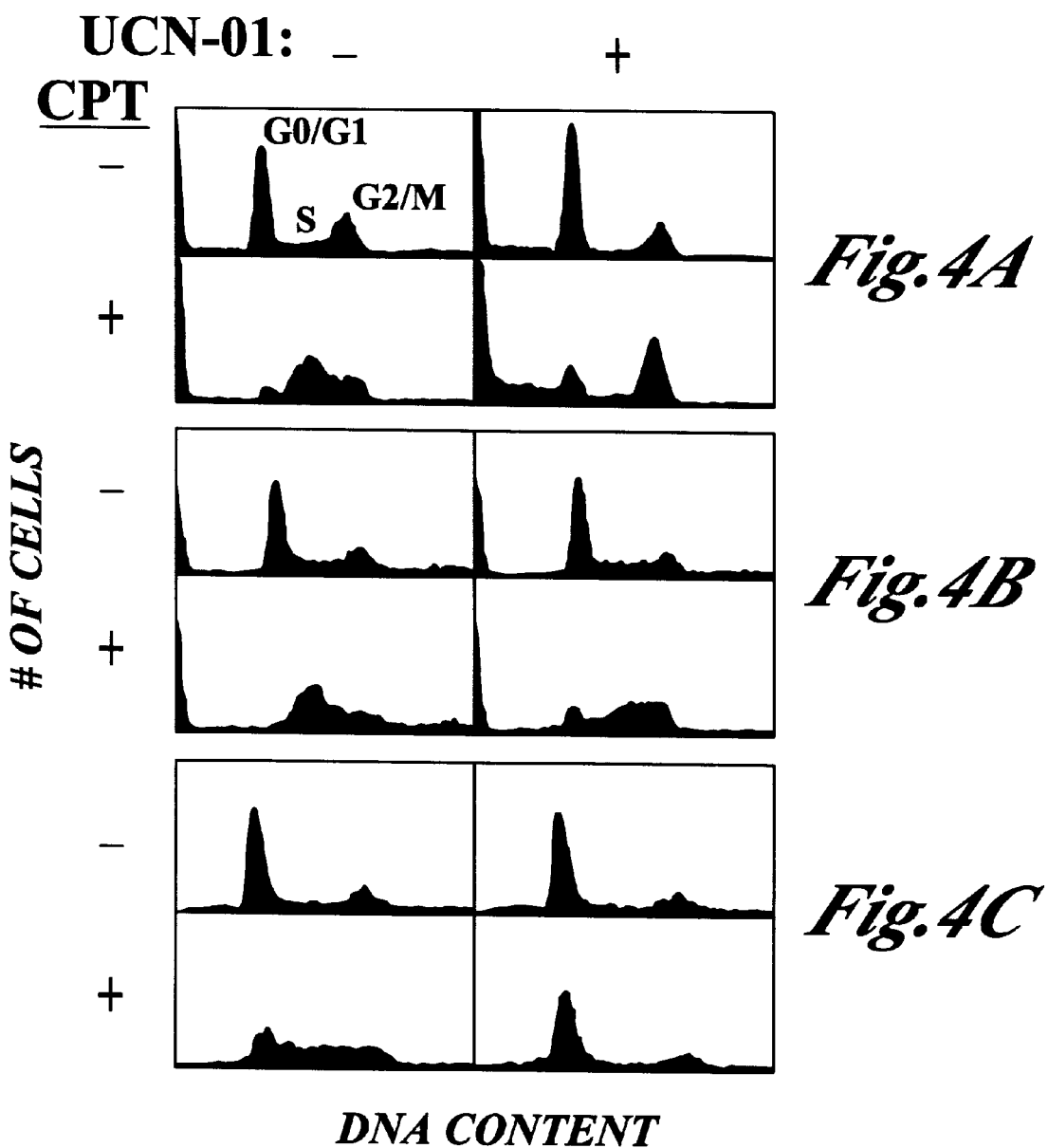
FIG. 4 shows the effect of UCN-01 on abrogation of CPT-induced S/$G_2$ checkpoint activation in GI 101A, MDA-231 and normal endothelial cells. Asynchronous cells were treated for 24 h with 100 nM CPT in the presence and absence of 100 nM UCN-01. Cells were fixed, stained with propidium iodide and analyzed by flow cytometry (FHCS) for DNA content. In tumor cells (FIGS. 4A and 4D: GI 101A and FIGS. 4B and 4E: MDA-231) the addition of UCN-01 caused acceleration of passage to mitosis and loss of cells from S phase. In contrast, normal endothelial cells (FIGS. 4C and 4F) arrested in $G_0/G_1$ phase with no acceleration of passage of cells from S phase to mitosis. The percentage of cell population in $G_0/G_1$ (■), S (▩) and $G_2/M$ (□) phases in response to drug treatment are the means±SE of at least two independent experiments.

To determine whether the synergistic interaction between CPT and UCN-01 is the result of abrogation of S/$G_2$ checkpoint activation, the effect of sublethal doses of UCN-01 on CPT-induced S phase arrest in tumor and normal cells was determined by flow cytometry. In these experiments, asynchronized cells were simultaneously treated for 24 h with 100 nM CPT, 100 nM UCN-01 and drug combination. Following incubation in drug-free medium for an additional 24 h, cells were then analyzed for cell cycle distribution (FIG. 4). As indicated previously, (see Jones C. B. et al., "Sensitivity to camptothecin of human breast cancer cells and normal bovine endothelial cells, in vitro," *Cancer Chemother. Pharmacol.* (in press, 1997)), the addition of 100 nM CPT caused an arrest of tumor as well as normal cells in S phase. However, when these cells were treated with 100 nM UCN-01, a different effect on the rate of passage of cells was observed. While 100 nM UCN-01 had little effect on any of the cell lines by itself, it had significant effects on CPT-induced S phase arrest. On normal cells, 100 nM UCN-01 eliminated the CPT-induced S phase accumulation, causing cells to accumulate in $G_0/G_1$ compared to CPT treated cells (FIGS. 4C and 4F). Although the response of MDA 231 cells to 100 nM CPT was similar to the normal endothelial cells, the response of the drug combination was quite different. Incubation of these cells with 100 riM UCN-01 shifted the CPT-induced S phase arrest later in the cell cycle, with no accumulation of cells in $G_0/G_1$ phase (FIGS. 4B and 4E). Further investigation is underway to determine if early mitosis is a result of this shift. Similar results were obtained when GI 101A cells were treated with the drug combination (FIGS. 4A and 4D). Interestingly, the drug combination in this case caused a much greater number of cells that stained with sub-$G_0/G_1$ phase amounts of DNA. This may be due to cells undergoing apoptosis or necrosis. Thus these data demonstrate that normal cells treated with sublethal doses of UCN-01 were protected against CPT-induced cytotoxicity by arresting in $G_0/G_1$ phase. In contrast, UCN-01 abrogated S phase arrested tumor cells that lack p53 function by accelerating the passage of cells to mitosis.

Discussion

The foregoing Examples 1–3 demonstrate the ability of UCN-01 to potentiate CPT-induced cytotoxicity in two human breast carcinoma cell lines defective for p53 function through modulation of CPT-activated S and $G_2$ checkpoints.

The sensitivity of cells to CPT treatment is determined by their ability to activate checkpoints in S and $G_2$ phases of the cell cycle (Jones C. B. et al., "Sensitivity to camptothecin of human breast cancer cells and normal bovine endothelial cells, in vitro," *Cancer Chemother. Pharmacol.* (in press, 1997); O'Connor P. M. et al., "S-phase population analysis does not correlate with the cytotoxicity of camptothecin and 10,11-methyldioxycamptothecin in human colon carcinoma HT-29 cells," *Cancer Commun.* 3:233–240 (1991); Dubrez L. et al., "The role of cell cycle regulation and apoptosis triggering in determining the sensitivity of leukemia cells to topoisomerase I and II inhibitors," *Leukemia* 9:1013–1024 (1995); and Wang Y. et al., "Down-regulation of DNA replication in extracts of camptothecin-treated cells: Activation of an S-phase checkpoint," *Cancer Res.* 57:1654–1659 (1997)). At low doses, CPT causes an accumulation of breast carcinoma cells that lack p53 function (MDA 231 and GI 101A) in the $G_2$ phase while at high doses cells are arrested in the S phase. This dual arrest is well correlated with the low and high levels of DNA-induced damage, respectively (Goldwasser F. et al., "Correlations between S and $G_2$ arrest and the cytotoxicity of camptothecin in human colon carcinoma cells," *Cancer Res.*

56:4430–4437 (1996)). Therefore, pharmacological modulation of events during the S and $G_2$ phases can potentially enhance the therapeutic index of CPT and analogs. This can simply happen by accelerating the progression of cells that lack p53 normal function through S phase, hence inducing early mitosis which can occur prior to sufficient repair of DNA damage in $G_2$. Normal cells that pass the $G_1$ checkpoint during this modulation would also progress to $G_2$ and would also be sensitive to modulation at $G_2$ phase. However, the wild-type p53 seems to protect these cells from abrogation at the S and $G_2$ checkpoints (Russell, K. J. et al., "Abrogation of the $G_2$ checkpoint results in differential radiosensitization of $G_1$ checkpoint-deficient and competent cells," *Cancer Res.* 55:1639–1642 (1995); Powell, S. N. et al., "Differential sensitivity of p53– and p53+ cells to caffeine-induced radiosensitization and override of $G_2$ delay," *Cancer Res.* 55:1643–1648 (1995)). This approach was tested in cultures with the use of UCN-01, a new $G_2$ abrogator (Russell K. J. et al., "Abrogation of the $G_2$ checkpoint results in differential radiosensitization of $G_1$ checkpoint-deficient and competent cells," *Cancer Res.* 55:1639–1642 (1995)).

UCN-01 (7-hydroxystaurosporine) (FIG. 1) is entering phase I clinical trials following evidence of preclinical activity (Akinaga S. et al., "Antitumor activity of UCN-01, a selective inhibitor of protein kinase C, in murine and human tumor models," *Cancer Res.* 51:4888–4892 (1991); and Lush R. M. et al., "Surprising pharmacokinetics of UCN-01 in patients with refractory neoplasms may be due to high degree of protein binding," *Proc. AACR* 38:4029 (1997)). The drug was originally isolated from a strain of Streptomyces as a protein kinase C (PKC)-selective inhibitor (Takahashi I. et al., "UCN-01, a selective inhibitor of protein kinase C from Streptomyces," *J Antibiot.* 40:1782–1784 (1987)), although recent evidence suggest that PKC inhibition is unlikely to be directly responsible for the UCN-01 cytotoxicity (Seynaeve C. M. et al., "Cell cycle arrest and growth inhibition by the protein kinase antagonist UCN-01 in human breast carcinoma cells," *Cancer Res.* 53:2081–2086 (1993); and Monks A. et al., "Synergistic interactions between UCN-01 and various anti-cancer agents in vitro: relationship to p53 function," *Proc. AACR* 38:2137 (1997)). UCN-01 has been shown to abrogate S and $G_2$ checkpoints following DNA damage, preferentially in cells with disrupted p53 function compared to wild-type p53. Thus when the drug was combined with radiation or cisplatin, a synergistic interaction was only observed in cells with disrupted p53 function (Russell, K. J. et al., "Abrogation of the $G_2$ checkpoint results in differential radiosensitization of $G_1$ checkpoint-deficient and competent cells," *Cancer Res.* 55:1639–1642 (1995); and Bunch R. T. et al., "Enhancement of cisplatin-induced cytotoxicity by 7-hydroxystaurosporine (UCN-01), a new $G_2$-checkpoint inhibitor," *Clinical Cancer Res.* 2:791–797 (1996)). The data from Examples 1–3 demonstrates that UCN-01 at sublethal doses can enhance CPT-induced cytotoxicity in tumor cells as compared to normal endothelial cells (FIG. 2). When this enhancement was assessed according to inhibition of cell growth, the $IC_{50}$ values obtained for CPT in the presence and absence of 100 nM UCN-01 during 24 exposure of GI 101A cells were 300 nM and 10 nM, respectively; and for MDA-231 cells were 200 nM and 5 nM (FIGS. 2A and 2B). There was no enhancement of CPT-induced cytotoxicity in normal endothelial cells as clearly indicated in FIG. 2C.

The potentiating effect of UCN-01 on CPT-induced cytotoxicity in tumor cells with disrupted p53 function raises the question as whether this phenomenon is additive or synergistic. To address this question, the outcome of the drug combination (growth and proliferation inhibition) was assessed using the median-effect analysis (Chou T-C. et al. "Quantitative analysis of dose-effect relationships: The combined effects of multiple drugs or enzyme inhibitors," *Adv. Enzyme Regul.* 22:27–55 (1984)). The antiproliferative activity (DNA synthesis) of CPT on breast cancer cells with disrupted p53 is more pronounced than its growth inhibition effect (Jones C. B. et al., "Sensitivity to camptothecin of human breast cancer cells and normal bovine endothelial cells, in vitro," *Cancer Chemother. Pharmacol.* (in press, 1997)). Thus when growth inhibition of the drug combination was analyzed a synergistic cytotoxic effect was clearly indicated in both cell lines, as shown in FIG. 3A; however, antagonistic interaction was observed with the antiproliferative activity of the drug combination (FIG. 3B). This effect indicates that UCN-01 is counteracting CPT-induced inhibition of DNA synthesis by increasing the rate of DNA synthesis in tumor cells. Thus the DNA content of treated cells was determined by flow cytometry (FIG. 4). As expected, UCN-01 is preferentially abrogating only the DNA damage dependent activation of $S/G_2$ checkpoint induced by CPT. Acceleration of the passage of the tumor cells through the S phase of the cell cycle was observed when cells were incubated with sublethal doses of UCN-01, thereby increasing the cytotoxic activity of CPT. This hypothesis is supported by the results of [$^3$H]-thymidine incorporation assays (FIG. 3B) that showed UCN-01 was able to eliminate suppression of DNA synthesis and thus antagonistic interaction was observed. While the normal endothelial cells showed a loss of S phase arrested cells with UCN-01 treatment, they accumulated in $G_0/G_1$ (FIG. 4C) and were relatively resistant to the cytotoxicity of the drug combination (FIG. 2C). This was as expected from normal cells expressed wild-type p53. Thus the cell cycle response of the normal cells to CPT and UCN-01 was markedly different than that of the tumor cells, and may be responsible for their lower drug sensitivity.

The molecular events responsible for the observed synergism between UCN-01 and CPT have not been fully established. One possible explanation of the results might be related to DNA damage dependent mechanisms and the components of cell cycle regulatory proteins. For example, the activity of cyclin-dependent kinases (cdk's) is known to be essential for progression through the cell cycle, but the specific substrates for those kinases, and the way they promote cell cycle progression remain a mystery. However, some molecules in the process have roles supported by enough evidence that conclusions can be made based on their status. Arrest of the cell cycle in the $G_2$ phase is likely regulated by the cyclin dependent kinase, $p34^{cdc2}$ (reviewed in Pines J., "Cyclins, cdks and cancer," *Semin. Cancer Biol.* 6:63–72 (1995).) The direct regulators of $p34^{cdc2}$ are wee1 kinase, that phosphorylates and inactivates $p34^{cdc2}$, and the cdc25 phosphatase, that activates $p34^{cdc2}$ (Raibowol K. et al., "The cdc2 kinase is a nuclear protein that is essential for mitosis in mammalian cells," *Cell* 57:393–401 (1989); and Strausfeld V., "Dephosphorylation and activation of a $p34^{cdc2/cyclin\ B}$ complex in vitro by human cdc25 protein," *Nature* 351:242–244 (1991)). Recent studies by Tsao et al., "The involvement of active DNA synthesis in camptothecin-induced $G_2$ arrest: altered regulation $p34^{cdc2/cyclin\ B}$," *Cancer Res.* 52:1823–1829 (1992), showed that CPT treatment led to a loss in activity of $p34^{cdc2}$ in HeLa cells. This inactivation was associated with $G_2$ arrest in these cells, however, cyclin B levels were maintained at a high level despite a decrease in the rate of cyclin B synthesis. It was also noticed that subsequent to CPT treatment, there was a loss in the dephosphorylation of p34$^{cdc2}$. This suggests that CPT was causing, either directly or indirectly the inactivation of p34$^{cdc2}$ by affecting its phosphorylation state, and this led to a $G_2$ arrest. While the precise mechanisms underlying the antitumor activity of UCN-01 remain unclear (Wang Q. et al., "Apoptosis in 7-hydroxystaurosporine-treated T lymphoblasts correlates with activation of cyclin-dependent kinase 1 and 2," *Cell Growth Differ.* 6:927–936 (1995)), demonstrated that UCN-01-induced apoptosis which correlated with inappropriate activation of cdk2 and p34$^{cdc2}$ in cultured T lymphoblasts. Thus it is possible that UCN-01 abrogates S and $G_2$ checkpoints by this activation. Furthermore, as cdk2 is active during S phase of the cell cycle (Pines J., "Cyclins, cdks and cancer," *Semin. Cancer Biol.* 6:63–72 (1995)), its inappropriate activation by UCN-01 may be enhancing progression through S phase as well. If this occurs, and if a failure to arrest at the $G_2$/M phase or slow DNA synthesis during S phase does increase DNA damage induced by CPT treatment, then UCN-01 could act synergistically with CPT. Furthermore, cells that lack other regulators of the cell cycle such as p53, there may be a greater increase in cytotoxicity with drug combination, due the lack of other checkpoints where the cell cycle could be arrested, and further DNA damage avoided or repaired. Alternate cdk inhibitors might be involved in these checkpoint controls, and alternative explanations are possible.

The foregoing examples demonstrate that UCN-01, an agent entering phase I clinical trial, can abrogate CPT-induced activation of S/$G_2$ checkpoint in breast tumor cells with mutant p53 gene. This abrogation occurred with the use of sublethal doses of UCN-01 and was correlated with enhancement of CPT-induced cytotoxicity in tumor cells. Normal endothelial cells which express normal p53 function were arrested in $G_0$/$G_1$ phase with no potentiation of CPT-induced cytotoxicity. Thus, the staurosporine analog UCN-01 enhances the therapeutic index of topoisomerase I inhibitors as a result of tumor specific differences at cell cycle checkpoints.

EXAMPLE 4

P53 Dependence of Abrogation of S and $G_2$ Arrested Cells

The hypothesis of the p53 dependence of the abrogation of S and $G_2$ arrested cells with mutant p53 by sublethal doses of UCN-01 and was tested CPT, using isogenic cells of human mammary epithelial cells (HMEC) transfected with HVP-16 E6 gene (HMEC/E6). These cells were obtained from Dr. Scott Foster of Fred Hutchison Cancer Research Center, Seattle, Wash. By transfecting HMEC with HVP-16, the loss of p53 from these normal cells was mimicked. These cells were used to explore the specific consequence of losing p53 from normal cells that otherwise were syngeneic with p53 wild type controls. Thus isogenic cells were used to confirm that any effect of UCN-01 is related to the p53 status.

Figure 5A:
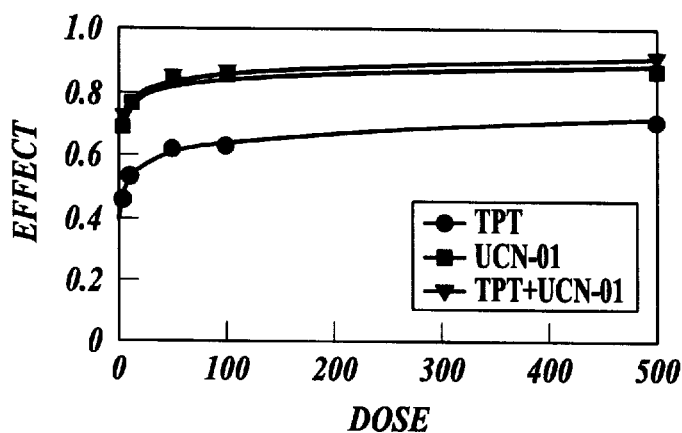
FIGS. 5A–5C show the dose effect of p53 disruption on the sensitivity of human mammary epithelial cells as compared to human MDA-231 breast carcinoma to topotecan (TPT) and UCN-01, as described in Example 4. Exponentially growing HMEC (p53+) (FIG. 5A), or HMEC/E6 (p53−) (FIG. 5B), or MDA-231 (mutant p53, FIG. 5C) cells were treated with topetecan (TPT, ●), UCN-01 (■), or combination at 1:1 molar ratio (▼) for 24 hr. Growth inhibition was assessed after five days using the crystal violet staining assay. Values shown are the mean of quadruplicate determinations.
Figure 5B:
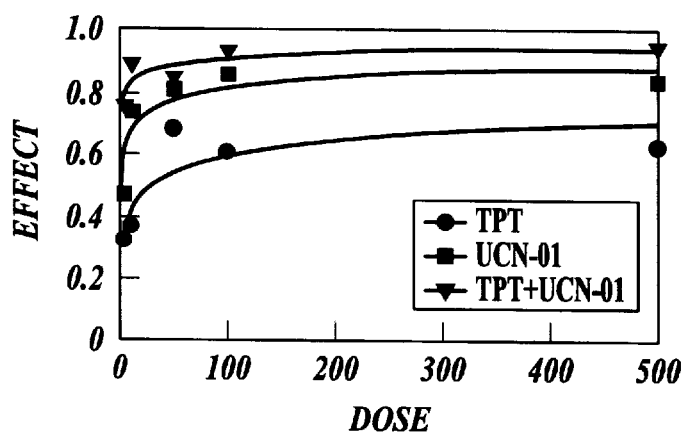
Figure 5C:
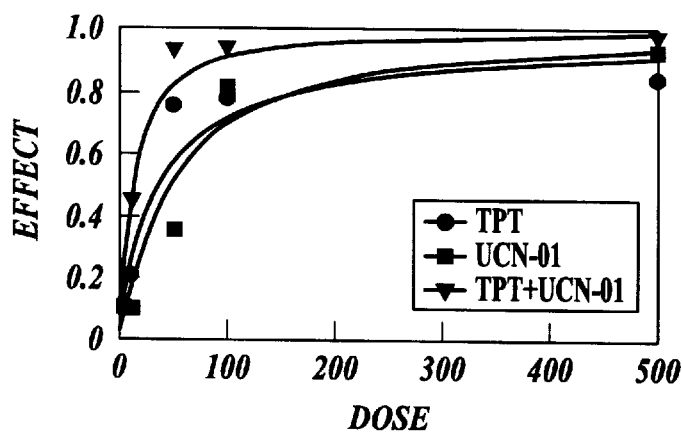
Figure 6A:
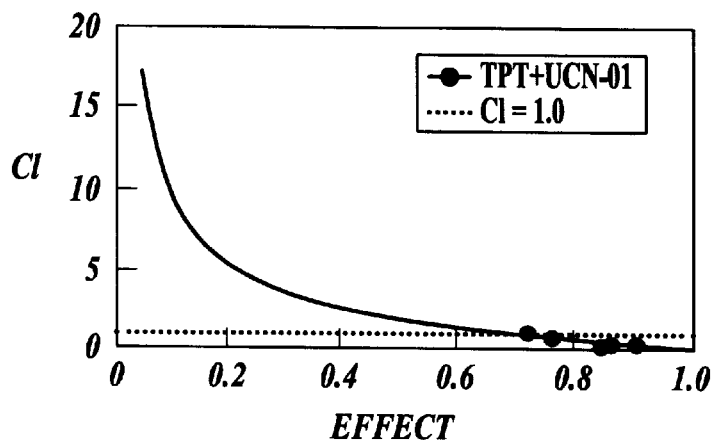
FIGS. 6A–6C are CI-effect plots of the cells and treatments of FIGS. 5A–5C, respectively, as described in Example 4, showing that the drug combination is truly synergistic with FIGS. 6B and 6C (CI<1.0) but not with FIG. 6A (CI>1.0). Thus UCN-01 enhances TPT-induced cytotoxicity in p53 dysfunction cells as compared to HME cells with normal p53 function.
Figure 6B:
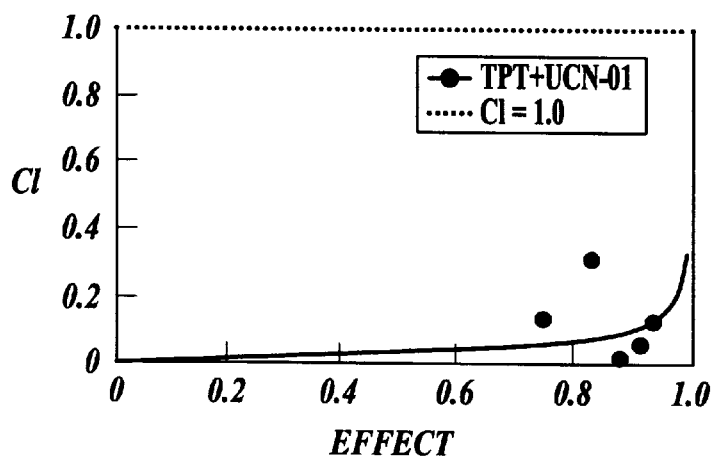
Figure 6C:
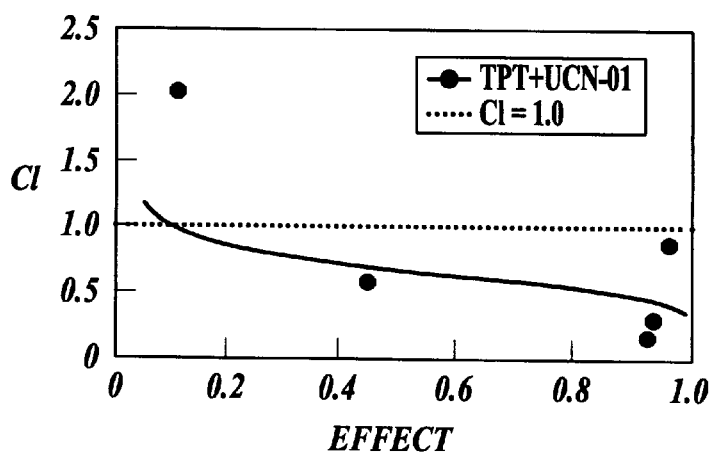

Cytotoxicity and Bromodeoxyuridine incorporation assays. For cytotoxicity, early passage cells (2–8 passage) were maintained in culture and plated in 24 well plates in mammary epithelial cell growth medium (MEGM, Biowhitaker, Walkersvile, Md.). Cultures of isogenic cells as well as MDA-231 tumor cells with mutated p53 were treated for 24 hr. with various concentrations of topotecan (TPT), UCN-01 and combination (1:1 ratio), followed by 3 days incubation in fresh medium. Growth inhibition as a function of relative cell number was determined by the crystal violet staining assay (Redkar, A. A. et al., "UCN-01 dose-dependent protective effect of normal tissue in mice," *Proc. AACR* 40:70, (1999)). The drug combination was then analyzed by the median effect analysis method of Chou T-C. et al., "Quantitative analysis of dose-effect relationships: The combined effects of multiple drugs or enzyme inhibitors," *Adv. Enzyme Regul.* 22:27–55 (1984), processed by a computer program developed by Chou and Chou (Biosoft). As shown in FIG. 5B where HMEC/E6 were incubated with TPT and then with various concentrations of UCN-01, there was a dramatic enhancement of growth inhibition (dose-effect plot) as indicated by the calculated IC$_{50s}$ (see Table 1 below). As shown in FIG. 6B, the drug combination is clearly synergistic (CI-effect plot) where CI<1.0. Similar results were obtained with the treatment of MDA-231 cells (FIGS. 5C and 6C). In contrast, normal HMEC with normal p53 function (FIGS. 5A and 6A) showed less effect to the drug combination than to UCN-01 treatment, and the interaction is antagonistic or additive at best. These data indicate that potentiation of TPT-induced cytotoxicity by UCN-01 is p53-dependent.

TABLE 1

IC$_{50s}$(nM) of HMEC, HMEC/E6 and MDA-231 treated with TPT, UCN-01 and combination

| Drug | HMEC (p53+) | HMEC/E6 (p53−) | MDA-231 (p53−) |
|---|---|---|---|
| TPT | 6.00 | 34.00 | 37.00 |
| UCN-01 | 0.07 | 1.40 | 49.60 |
| Combination (1:1) | 0.13 | 0.048 | 14.30 |

EXAMPLE 5

Cell Proliferation Assay

We next asked whether UCN-01 enhances TPT-induced cytotoxicity through modulation of cellular DNA synthesis or other mechanisms are involved. Earlier we showed that CPT-resistant cells stopped incorporating $^3$H-thymidine at low doses of CPT, while CPT-sensitive cells continued to incorporate $^3$H-thymidine at very high doses. For the quantification of cell proliferation and the effect of UCN-01 on TPT-induced inhibition of DNA synthesis, we used the calorimetric ELISA BrdU incorporation assay (Boehringer Mannheim). MDA-231 cells were treated for 24 hr with individual drugs (10 nM and 50 nM) and drug combination (1:1 molar ratio) followed by 3 hr pulse with BrdU (10 $\mu$M). Cells were then assayed for BrdU incorporation using the antibody conjugate (BrdU-POD) and measuring absorbence at 450 nm, as recommended by the manufacturer. As indicated in FIG. 7, the MDA-231 cells stopped incorporating BrdU at 10 and 50 nM doses of TPT. These doses are well below cytotoxic concentrations as measured by the crystal violet staining assay (FIG. 5C). It is possible that the lose of BrdU incorporation in response to TPT treatment, protects the cells from the cytotoxic effect of the drug. Incubation in sublethal doses of UCN-01 (10 nM and 25 nM) antagonized the ability of the cells to stop incorporating BrdU, and this antagonism is correlated with the cytotoxic synergism seen in these cells (FIGS. 5C, 6C). Thus it appears likely that the mechanism of interaction between the two drugs is due to the ability of UCN-01 to abrogate the protective arrest of BrdU incorporation seen in the malignant cells in response to TPT treatment.

EXAMPLE 6

DNA Synthesis Assay

The rate of DNA synthesis in TPT and UCN-01 treated cells was further investigated by a simultaneous assessment of cell cycle phase (propidium iodide) and DNA synthesis (fluorescein-conjugated anti-bromodeoxyuridine antibody). Incorporation of BrdU into cells allows visualization of cells activity synthesizing DNA and thus permits an accurate measurement of the cell population going through S phase. Asynchronized MDA-231 cells were treated with various concentrations of TPT or UCN-01 (10,50,100 nM) or simultaneous combination of TPT doses+25 nM UCN-01 for 24 h., fixed, stained with propidium iodide (PI) and analyzed by FACS for DNA content, as we described above (see Example 3 and FIG. 4). For two-parameter analysis of cell cycle progression, cells were continuously cultured with 10 $\mu$M BrdU for 4 hr before harvesting. Cells were fixed, denatured and stained with anti-BrdU/FITC (Boehringer Mannheim) for 45 min, treated with RNase then stained with PI for flow cytometric analysis. The distribution of green fluorescence from FITC expressed on a logarithmic scale was collected as a measure of BrdU content, and distribution of red fluorescence from PI on a linear scale was collected as a measure of DNA content. Filters used were 550-nm dichroic, 525-nm band pass for green fluorescence and 585-nm band pass for red fluorescence. As with the case of CPT, TPT by itself induced an accumulation of MDA-231 cells in S phase (FIG. 8A), while UCN-01 causes $G_1$ arrest (FIG. 8B). The percentage of the cell population in $G_1$, S, and $G_1/_M$ phases in response to the drug treatment is shown in FIGS. 9A–9C. When used in combination with TPT, UCN-01 eliminated TPT-induced S phase arrest, causing an acceleration of passage of cells to $G_2$ for early mitosis. These results suggest that sublethal doses of UCN-01 can indeed abrogate S phase arrested cells with mutated p53.

EXAMPLE 7

Effect of UCN-01 on Murine Intestinal Epithelium and Bone Marrow Cells

This example tests the hypothesis that preincubation of non-transformed cells with UCN-01 should arrest them in $G_1$ so that they are now resistant to anticancer agents. UCN-01 might protect normal cells from DNA damaging agents such as topoisomerase inhibitors which require S phase passage for their efficacy. Thus, possible suppression of hyperproliferative cells in the epithelial lining of the gut and bone marrow by UCN-01 was investigated. Six to eight weeks C57/BL mice were divided into five different groups (n=3/group) and injected i.m. with a single dose of UCN-01 (0–20 mg/kg) followed by in vivo BrdU (20 mg/kg) labeling for 1 h. At autopsy (3 or 24 hr following drug administration) bone marrow was fixed for dual parameter BrdU/DNA flow cytometry and different regions of the gut namely: (1) duodenum, (2) jejunum, (3) ileum, and (4) colon/rectum were fixed for immunoperoxidase BrdU assay. Counterstaining was performed by hematoxyline and controls included sections stained without the primary antibody. Cells undergoing DNA replication during the hour prior to sacrifice stained brown. Specific brown reaction product was seen localized on the nuclei of epithelial cells in the luminal crypts and is indicative of proliferating cells while the negative cells stained blue with hematoxyline. A variable number of proliferating epithelial cells were identified in the first three regions and much lesser cells in the fourth region of the gut. Sections were analyzed by an image analysis system using thresholding techniques and sampled for using percentage black and white areas. From each segment of the gut, 5 areas were scored and averaged to obtain the mean values±SE vs. dose. The image was collected from an BH-2 Olympus microscope with a black and white TULNIS CCD camera and brought into NIH Image 1.61 on a quadra 950 Mac computer for analysis. A comparison between groups showed that UCN-01-induced suppression in BrdU positive cells in a dose-dependent manner at both 3 and 24 hr following drug administration.

As shown in FIG. 10A, UCN-01 causes a significant suppression in hyperproliferative cells in all gut segments at 5 mg/kg as compared to controls. This effect was also true in mice treated with UCN-01 for 24 hr, as shown in FIG. 10B. Death of animals injected with doses higher than 5 mg/kg was observed. As a consequence, UCN-01 caused an increase in the DNA replication process with 10 mg/kg, hence hyperproliferation of intestinal epithelial cells (FIG. 10A).

For dual parameter BrdU/DNA flow cytometry of the murine bone marrow (FIGS. 11A, 11B, and 11C), cells were stained with antiBrdU and FITC conjugated antibody+PI, as mentioned before. This proliferation/cell cycle assay is an accepted method of quantitation of $G_1$/S arrest, as determined by dividing the calculated $G_1$:S ratio of the treated cells by $G_1$:S ratio of untreated cells (Daoud, S. S. et al., "Antitumor effects of liposome-incorporated camptothecin in human tumor xenografts," *Anti-Cancer Drugs* 6: 83:92 (1995)).

As shown in FIGS. 11A, 11B, 11C and 11D mice treated with 5 mg/kg UCN-01 resulted in $G_1$/S arrest of the bone marrow cells as determined by the above mentioned formula. The calculated $G_1$/S arrest were 2.09 and 1.17 for 3 hr and 24 hr treatment, respectively. These data indicate that suppression of proliferation in these two normally hyperproliferating tissues by low doses of UCN-01 may predict protection from intestinal and bone marrow toxicity of TPT.

EXAMPLE 8

In Vitro Bone Marrow Cell Protection Assay

Thus in vitro protection assay on murine bone marrow cells was initiated. In this experiment, murine bone marrow cells were obtained from the femurs of 6–8 weeks old C57/BL mice. Single cell suspension was prepared by gentle pipetting, and viable cells were counted using a hemocytometer. The bone marrow cells were diluted to $1.5 \times 10^5$ cells/ml in DMEM+2% FBS. For duplicate cultures, 0.3 ml of cell suspension was treated with TPT (0–1000 nM) or UCN-01 (0–1000 nM) or with the drug combination (1:1 molar ratio) and added to 3 ml methylcellulose medium (Methocult™, Stem Cell Technologies) where 1.1 ml of this suspension was dispensed to each of the two 35 mm culture dishes. The dishes were incubated at 37° C. in a fully humidified atmosphere of 5% $CO_2$ in air for 12–14 days. CFU-GM colonies were counted under inverted microscope as multicellular aggregates of 50$\mu$ or greater in diameter. Results were expressed as % effect vs. dose, and the level of drug interaction was determined by the median effect analysis method of Chou T-C. et al., "Quantitative analysis of dose-effect relationships: The combined effects of multiple drugs or enzyme inhibitors," *Adv. Enzyme Regul.* 22:27–55 (1984), processed by a computer program developed by Chou and Chou (Biosoft). As shown in FIG. 12B, the CI-effect plot the interaction of TPT+UCN-01 on the bone marrow cells is clearly antagonistic (CI>1), the calculated $IC_{50s}$ for TPT, UCN-01 or drug combination are 19 nM, 44.5 nM and >44.5 nM, respectively. In summary, the data presented herein demonstrates that low doses of UCN-01 suppress the hyperproliferative cells of the normal tissues of the gut and bone marrow cells, and the interaction of TPT+UCN-01 on murine bone marrow cells is antagonistic as determined by the colongenic assay for CFU-GM.

EXAMPLE 9

Pharmacokinetics

Recent Phase I clinical trials at the NCI indicated that UCN-01 displayed high plasma concentrations and a long half-life in patients following 72- or 3-h infusion. Extremely low systemic clearance and small distribution volume of the drug was attributed to the high affinity binding to $\alpha_1$-acid glycoprotein (AGP) (Foster, S. A. et al., "The ability of human papillomavirus E6 proteins to target p53 for degradation in vivo correlates with their ability to abrogate actinomycin D-induced growth arrest," *J. Virol.* 68:5698–5705 (1994)). Many basic drugs tend to bind in variable degrees to AGP (Knowlton, K. et al., "Bcl-2 slows in vitro breast cancer growth despite its antiapoptotic effect," *J. Surg. Res.* 76:22–26 (1998)). The levels of AGP are greatly increased in a variety of pathological conditions such as trauma, inflammatory reaction, myocardial infarction and cancer. Thus monitoring changes in the pharmacokinetic drug concentrations in these pathological conditions is extremely important, since dosage adjustment would be considered. For our drug combination, this binding is of a crucial consequence since the attainable plasma and tumor concentrations may be questionable and plasma protein displacement interaction may occur and can lead to undesirable side effects. Thus the role of human $\alpha_1$-acid glycoprotein (AGP) binding on UCN-01 disposition was determined. In this example, two groups of rats were prepared by cannulating the femoral vein and artery. The first group (n=6) received UCN-01 (10 mg/kg i.v.) by slow infusion over 1 min., while the second group (n=5) received UCN-01+10 mg human $\alpha_1$-acid glycoprotein. Plasma samples were obtained over time (0–700 min), and were analyzed for UCN-01 by HPLC system (Shimazdu LC), detecting peaks using fluorescence detector (excitation=310 nm, emission=410). As shown in FIG. 13, the plasma concentration-time profile declined biexponentially after the two treatments, however, the plasma concentrations were significantly higher after administration of UCN-01+ human AGP. Non-linear regression analysis using PCNONLIN showed that the $t_{1/2}\alpha$ and the $t_{1/2}\beta$ in the two groups ranged from 11.00–51.00 min. and 399–417 min., respectively (FIG. 13). Human AGP administration significantly decreased UCN-01 volume of distribution during the elimination phase from 6.8 L/kg after UCN-01 administration alone to 1.7 L/kg after co-administration with human AGP. This also resulted in a significant reduction of UCN-01 total body clearance from 0.26 L/hr after UCN-01 alone to 0.09 L/hr after co-administration with human AGP. Although the presence of human AGP resulted in significant reduction of both the volume of distribution and total body clearance of UCN-01, yet peak plasma concentration>100 nM was attainable and lasted up to 300 min.

EXAMPLE 10

Effect of AGP

The role of human AGP binding on the tissue distribution of UCN-01. In this study, two groups of rats (n=3) were infused with bolus injection of either UCN-01 (10 mg/kg) or UCN-01+ human AGP (10 mg/kg +10 mg). On hour following drug administration, plasma samples as well as organ tissues (brain, muscle, kidneys, lungs, liver, heart and spleen) were collected. Tissues were digested and homogenized, protein was precipitated with cold ethanol/1% ascorbic acid, and the supernatant was extracted with chloroform. The organic phase was then dried under nitrogen, reconstituted in acetonitrile and analyzed by HPLC as mentioned above. The results are shown in Table 2.

TABLE 2

Tissue Distribution of UCN-01 in male Wistar rats
(n = 3 rats/group, Mean ± SD)

| | UCN-01 | | UCN-01 + human AGP | |
| --- | --- | --- | --- | --- |
| Tissue | ng/g tissue | Tissue/Plasma | ng/g tissue | Tissue/Plasma |
| Plasma | 240 ± 35 ng/ml | | 2964 ± 250 ng/ml | |
| Brain | 2446 ± 495 | 10.49 ± 1.9 | 1720 ± 78.4 | 0.6 ± 0.33 |
| Muscle | 11913 ± 783 | 60 ± 5.48 | 6586 ± 3057 | 2.27 ± 1.11 |
| Heart | 19920 ± 9945 | 86.8 ± 41.7 | 10146 ± 4898 | 3.5 ± 1.7 |
| Liver | 42853 ± 3210 | 189 ± 131 | 30080 ± 2528 | 11.3 ± 1.34 |
| Kidney | 73173.3 ± 3050 | 298 ± 40 | 39353 ± 8511 | 14 ± 5.6 |
| Spleen | 74880 ± 5170 | 325.5 ± 208 | 53286 ± 3125 | 19.6 ± 14.7 |
| Lung | 279273 ± 19635 | 1191 ± 775 | 141333.3 ± 12046 | 53.65 ± 5.4 |

As shown in Table 2, the plasma concentration after the administration of UNC-01+ human AGP was significantly higher than UCN-01 alone. However, the tissue:plasma ratios of UCN-01 were significantly higher (10–1191 fold) especially in the deep tissue compartments as in the lung. Higher tissue:plasma ratio was maintained even in the presence of human AGP in all organ tissues except the brain. The very high concentration of UCN-01 in lung tissue suggests that this compound may be highly effective in the treatment of lung cancers. Thus this example indicates that the tissue distribution of UCN-01 is not significantly affected by the presence of human AGP and that higher plasma concentration is probably needed to achieve high tumor:plasma ratio or 100 nM tumor concentration of UCN-01 in the presence of human AGP.

EXAMPLE 11

CPT/TPT Plasma Concentration Profiles

The plasma-concentration time profile of TPT was also determined to evaluate the level of detection when used in combine drug therapy with UCN-01. FIG. 14, depicts a typical kinetic profiles of CPT and TPT following intravenous administration of 10 mg/kg of the drug to normal rats. In these experiments, plasma sample (100 µl) was diluted with 50 µl of McIlvaine's buffer, pH 7.4 followed by addition of 20 μl of methanol: acetonitrile mixture (1:2, v/v). The mixture was mixed and centrifuged for 2 minutes. A sample of 20 μl was immediately injected into the HPLC. The mobile phase of CPT analysis consists of 25% acetonitrile in 50 mM monobasic ammonium phosphate, and the flow rate is 0.5 ml/min. Separation was achieved on a Supelcosil ABZ+ column. The column effluent was monitored by fluorescence detector operated at excitation/emission wavelength of 380/520. The peak height were used for quantitation. The plasma concentration-time profiles of CPT and TPT, as shown in FIG. 7, declined biexponentially. The two drugs were distributed to all tissues then eliminated with $t_{1/2}$ of 85, and 92 min. for CPT and TPT, respectively. This analysis can be used to simultaneously quantitate CPT in the open and closed forms. TPT was analyzed using the same procedures except that the mobile phase consists of 14% acetonitrile in 50 mM ammonium phosphate, and the detector wavelength was adjusted to 370/435 for excitation/emission. The drug concentration was determined from the standard curve constructed by plotting the peak height ratios of CPT and/or TPT to the internal standard against known drug concentrations.

While the preferred embodiment of the invention has been illustrated and described, it will be appreciated that various changes can be made therein without departing from the spirit and scope of the invention.

REFERENCES

1. Dancey J and Eisenhauer E A. "Current perspectives on camptothecins in cancer treatment." *Br. J. Cancer* 74:327–338 (1996).

2. Sinha B K. "Topoisomerase I inhibitors: A review of their therapeutic potential in cancer." *Drugs* 49:11–16 (1995).

3. Darzynkiewicz Z, Bruno S, Del Bino G and Traganos F. "The cell cycle effects of camptothecins." In: Pantazis P, Giovanella B C, Rothenberg M L (eds). *The camptothecins from discovery to the patient*. The New York Academy of Sciences, New York, vol. 803, pp. 93–101 (1996).

4. D'Apra P, Beardmore C and Liu L F. "Involvement of nucleic acid synthesis in cell killing mechanisms of topoisomerase poisons." *Cancer Res.* 50:6919–6924 (1990).

5. Ryan A J, Squires S, Strutt H L, and Johnson R T. "Camptothecin cytotoxicity in mammalian cells is associated with the interaction of persistent double strand breaks in replicating DNA." *Nucleic Acid Res.* 19:3295–3300 (1991).

6. Jones C B, Clements M K, Wasi S and Daoud S S. "Sensitivity to camptothecin of human breast cancer cells and normal bovine endothelial cells, in vitro." *Cancer Chemother. Pharmacol.* (in press, 1997).

7. O'Connor P M, Nieves-Neira W, Kerrigan D, Bertrand R et al. "S-phase population analysis does not correlate with the cytotoxicity of camptothecin and 10,11-methyldioxycamptothecin in human colon carcinoma HT-29 cells." *Cancer Commun.* 3:233–240 (1991).

8. Dubrez L, Goldwasser F, Genne P, Pommier Y and Solary E. "The role of cell cycle regulation and apoptosis triggering in determining the sensitivity of leukemia cells to topoisomerase I and II inhibitors."*Leukemia* 9:1013–1024 (1995).

9. Wang Y, Perrault A R and Iliakis G. "Down-regulation of DNA replication in extracts of camptothecin-treated cells: Activation of an S-phase checkpoint." *Cancer Res.* 57:1654–1659 (1997).

10. Goldwasser F, Shimizu T, Jackman J, Hoki Y, O'Conner P M et al. "Correlations between S and $G_2$ arrest and the cytotoxicity of camptothecin in human colon carcinoma cells." *Cancer Res.* 56:4430–4437 (1996).

11. Hartwell L H and Weinert T A. "Checkpoints: controls that ensure the order of the cell cycle events." *Science* 246:629–634 (1989).

12. Kastan M B, Onyekwere O, Sidransky D, Vogelstein B and Graig R W. "Participation of p53 protein in the cellular response to DNA damage." *Cancer Res.* 51:6304–6311 (1991).

13. Kuerbitz S J, Plunkett B S, Walsh W V, and Kastan M B. "Wild-type 53 is a cell cycle checkpoint determinant following irradiation." *Proc. Natl. Acad Sci. USA* 89:7491–7495 (1992).

14. Barlogie B and Drewinko B. "Cell cycle stage-dependent induction of $G_2$ phase arrest by different antitumor agents." *Eur. J. Cancer* 14:741–745 (1978).

15. Soreson C M and Eastman A. "Influence of cis-diamminedichloroplatinum(II)-induced cytotoxicity: role of $G_2$ arrest and DNA double-strand breaks." *Cancer Res.* 48:4484–4488 (1988).

16. Lane, D P. "p53, guardian of the genome." *Nature* (Lond.) 358:15–16 (1992).

17. Fan S, El-Deiry W S, Bae I, Freeman J, Jondle D, Bhatia K, Forance A J, Magrath I, Kohn K W and O'Connor P M. "p53 gene mutations are associated with decreased sensitivity of human lymphoma cells to DNA damaging agents." *Cancer Res.* 54:5824–5830 (1994).

18. Lee J M and Bernstein A. "p53 mutations increase resistance to ionizing radiation." *Proc. Natl. Acad. Sci. USA* 90:5742–5746 (1993).

19. Lowe S W, Bodis S, McClatchey A, Remington L, Ruley H E, Fisher D E, Housman D E and Jacks T. "p53 status and the efficacy of cancer therapy in vivo." *Science* (Washington D.C.) 266:807–810 (1994).

20. Russell, K J, Wiens, L W, Galloway, D A and Groudine, M. "Abrogation of the $G_2$ checkpoint results in differential radiosensitization of $G_1$ checkpoint-deficient and competent cells." *Cancer Res.* 55:1639–1642 (1995).

21. Powell, S N, DeFrank, J S, Connell, P, Eogan, M, Preffer, F, Dombkowski, D, Tang, W and Friend S. "Differential sensitivity of p53– and p53+ cells to caffeine-induced radiosensitization and override of $G_2$ delay." *Cancer Res.* 55:1643–1648 (1995).

22. Russell K J, Wiens L W, Galloway D A, and Groudine M. "Abrogation of the $G_2$ checkpoint results in differential radiosensitization of $G_1$ checkpoint-deficient and competent cells." *Cancer Res.* 55:1639–1642 (1995).

23. [duplicate with #21] Powell S N, DeFrank J S, Connell P, Eogan M, Preffer F, Dombkowski D, Tang W and Friend S. "Differential sensitivity of p53– and p53+ cells to caffeine-induced radiosensitization and override of $G_2$ delay." *Cancer Res.* 55:1643–1648 (1995).

24. Fan S, Smith L M, Rivett, J D, Duba D, Zhan Q, Kohn W K, Fornace J A, and O'Connor M P. "Disruption of p53 function sensitizes breast cancer MCF-7 cells to cisplatin and pentoxifylline." *Cancer Res.* 55:1649–1654 (1995).

25. Bunch R T and Eastman A. "Enhancement of cisplatin-induced cytotoxicity by 7-hydroxystaurosporine (UCN-01), a new $G_2$-checkpoint inhibitor." *Clinical Cancer Res.* 2:791–797 (1996).

26. Wang Q, Fan S, Eastman A, Worland P J, Sausville E A and O'Connor P M. "UCN-01: a potent abrogator of $G_2$ checkpoint function in cancer cells with disrupted p53." *JNCI* 88:956–965 (1996).

27. Jones C B, Clements M K, Wasi S and Daoud S S. "Synergy between UCN-01 and camptothecin-induced cytotoxicity in breast cancer cells." *Proc. AACR* 38:102 (1997).

28. Daoud S S and Juliano R L. "Modulation of doxorubicin resistance by valinomycin (NSC 122023) and liposomal valinomycin in Chinese hamster ovary cells." *Cancer Res.* 49:2661–2667 (1989).

29. Daoud S S and Forde N H. "Synergistic cytotoxic actions of cisplatin and liposomal valinomycin on human ovarian carcinoma cells." *Cancer Chemother. Pharmacol.* 28:370–376 (1991).

30. Chou T-C and Talalay P. "Quantitative analysis of dose-effect relationships: The combined effects of multiple drugs or enzyme inhibitors." *Adv. Enzyme Regul.* 22:27–55 (1984).

31. Akinaga S, Gomi K, Morimoto M, Tamaoki T and Okabe M. "Antitumor activity of UCN-01, a selective inhibitor of protein kinase C, in murine and human tumor models." *Cancer Res.* 51:4888–4892 (1991).

32. Lush R M, Senderowicz A, Figg W D, Headlee D, Inoue K and Sausville E A. "Surprising pharmacokinetics of UCN-01 in patients with refractory neoplasms may be due to high degree of protein binding." *Proc. AACR* 38:4029 (1997).

33. Takahashi I, Kobayashi E, Asano K, Yoshida M and Nakano H. UCN-01, a selective inhibitor of protein kinase C from Streptomyces." *J. Antibiot.* 40:1782–1784 (1987).

34. Seynaeve C M, Stetler-Stevenson M, Sebers S, Kaur G, Sausville E A and Worland J P. "Cell cycle arrest and growth inhibition by the protein kinase antagonist UCN-01 in human breast carcinoma cells." *Cancer Res.* 53:2081–2086 (1993).

35. Monks A, Vaigro-Wolf A, Hose C, Sausville E A and O'Connor P M. "Synergistic interactions between UCN-01 and various anti-cancer agents in vitro: relationship to p53 function." *Proc. AACR* 38:2137 (1997).

36. Pines J. "Cyclins, cdks and cancer." *Semin. Cancer Biol.* 6:63–72 (1995).

37. Raibowol K, Draetta G, Brizuela L, Vandre D and Beach D. "The cdc2 kinase is a nuclear protein that is essential for mitosis in mammalian cells." *Cell* 57:393–401 (1989).

38. Strausfeld V. "Dephosphorylation and activation of a $p34^{cdc2/cyclin\ B}$ complex in vitro by human cdc25 protein." *Nature* 351:242–244 (1991).

39. Tsao Y P, D'Arpa P, Liu L F. "The involvement of active DNA synthesis in camptothecin-induced $G_2$ arrest: altered regulation $p34^{cdc2/cyclin\ B}$." *Cancer Res.* 52:1823–1829 (1992).

40. Wang Q, Worland P J, Clark J L, Carlson B A and Sausville E A. "Apoptosis in 7-hydroxystaurosporine-treated T lymphoblasts correlates with activation of cyclin-dependent kinase 1 and 2." *Cell Growth Differ.* 6:927–936 (1995).

41. Foster, S. A., Demers, G. W., Etscheid, B. G. and Gallway, D. A. The ability of human papillomavirus E6 proteins to target p53 for degradation in vivo correlates with their ability to abrogate actinomycin D-induced growth arrest. *J. Virol.* 68:5698–5705, 1994.

42. Redkar, A. A. and Daoud, S. S. UCN-01 dose-dependent protective effect of normal tissue in mice. *Proc. AACR* 40:70, 1999 (appended).

43. Daoud, S. S., Fetouh, M. I. and Giovanella, B. C. Antitumor effects of liposome-incorporated camptothecin in human tumor xenografts. *Anti-Cancer Drugs* 6:83:92 (1995).

44. Knowlton, K., Mancini, M., Creason, S., Morales, C., Hockenbery, D. and Anderson, B. Bcl-2 slows in vitro breast cancer growth despite its antiapoptotic effect. *J. Surg. Res.* 76:22–26, 1998.

The embodiments of the invention in which an exclusive property or privilege is claimed are defined as follows:

1. A composition for inhibiting the growth of breast cancer cells lacking normal p53 function comprising an enhanced effective amounts of a topoisomerase I inhibitor selected from the group consisting of camptothecin, topotecan, irinotecan and 9-aminocamptothecin; 7-hydroxystaurosporine; and a pharmaceutically acceptable carrier; wherein the amounts of the topoisomerase I inhibitor and 7-hydroxystaurosporine are effective to inhibit the growth of the breast cancer cells while protecting normal cells from topoisomerase I induced cytotoxicity.

2. The composition of claim 1, wherein the topoisomerase I inhibitor is camptothecin or topotecan.

3. A method for inhibiting the growth of breast cancer cells lacking normal p53 function comprising an enhanced effective amounts of contacting the cells with a composition comprising a topoisomerase I inhibitor selected from the group consisting of camptothecin, topotecan, irinotecan and 9-aminocamptothecin; and 7-hydroxystaurosporine; wherein the amounts of the topoisomerase I inhibitor and 7-hydroxystaurosporine are effective to inhibit the growth of the breast cancer cells while protecting normal cells from topoisomerase I induced cytotoxicity.

4. The method of claim 3, wherein the topoisomerase I inhibitor is camptothecin or topotecan.

5. A method of inhibiting the growth of breast tumor cells lacking normal p53 function in a patient comprising administering to the patient an enhanced effective amounts of a topoisomerase I inhibitor selected from the group consisting of camptothecin, topotecan, irinotecan and 9-aminocamiptothecin; and 7-hydroxystaurosporine to obtain inhibition of the growth of the tumor cells while protecting normal cells of the patient from topoisomerase I induced cytotoxicity.

6. The method of claim 5 wherein the 7-hydroxystaurosporine is administered to the patient before, during or after administration of the topoisomerase I inhibitor to the patient.

7. The method of claim 5 wherein from about 0.1 to about 300.0 mg of the topoisomerase I inhibitor/$m^2$ of body surface area is administered to the patient per day.

8. The method of claim 7 wherein the topoisomerase I inhibitor is administered to the patient for about one to about five consecutive days.

9. The method of claim 5 wherein from about 0.5 to about 15 mg of 7-hydroxystaurosporine/$m^2$ of body surface area is administered to the patient per day.

10. the method of claim 5, wherein the topoisomerase I inhibitor is camptothecin or topotecan.

* * * * *

UNITED STATES PATENT AND TRADEMARK OFFICE
CERTIFICATE OF CORRECTION

PATENT NO. : 6,214,821 B1
DATED : April 10, 2001
INVENTOR(S) : S.S. Daoud

It is certified that error appears in the above-identified patent and that said Letters Patent is hereby corrected as shown below:

Title page,
Item [56], References Cited, OTHER PUBLICATIONS,
"Dancey, J. and E.A. Eisenhauer" reference, "campthothecins" should read
-- camptothecins --
"Dubrez et al.," reference, "9:1013-1014" should read -- 9:1013-1024 --
"Knowlton et al.," reference, "Iits" should read -- Its --
Item [57], ABSTRACT,
Line 7, "an cell" should read -- a cell --

Column 1,
Line 3, after the title, insert the following paragraph:
-- This invention was made in part with government
support under grant CA 67265 awarded by the
National Institutes of Health. The government has
certain rights in the invention. --

Column 2,
Line 30, "agent" should read -- agents --
Lines 61-62, "methylx-
          anthines" should break as follows:
          -- methyl-
          xanthines --

Column 3,
Line 23, after "inhibit" delete ","

Column 4,
Line 54, "topetecan" should read -- topotecan --

Column 5,
Line 5, "with respect too" should read -- with respect to --
Line 42, "synergyanalysis" should read -- synergy analysis --
Line 51, "i. v." should read -- i.v. --

Column 6,
Lines 55-56, [U.S. Pat. No.] "5,004,
          758," should not break
Line 59, "As use herein" should read -- As used herein --

UNITED STATES PATENT AND TRADEMARK OFFICE
CERTIFICATE OF CORRECTION

PATENT NO.     : 6,214,821 B1
DATED          : April 10, 2001
INVENTOR(S)    : S.S. Daoud It is certified that error appears in the above-identified patent and that said Letters Patent is hereby corrected as shown below:

Column 8,
Line 25, "carnptothecin" should read -- camptothecin --

Column 9,
Line 26, after "such as" delete ","
Lines 49-50, "endot-
      helial" should break as follows:
      -- endo-
      thelial --

Column 10,
Line 26, "(Coming-Costar," should read -- (Corning-Costar, --
Line 33, "calorimetric" should read -- colorimetric --

Column 12,
Line 24, "riM" should read -- nM --
Lines 66-67, "camptoth-
      ecin" should break as follows:
      -- campto-
      thecin --

Column 13,
Line 35, "evidence suggest" should read -- evidence suggests --

Column 14,
Line 1, "as whether" should read -- as to whether --
Line 36, "cells expressed wild-type" should read -- cells expressing wild-type --
Line 54, "(1995)." should read -- (1995)). --
Lines 59-60, "$p34^{cdc2/}$
      $cyclin\ B$" should not break and should read as
      follows: -- $p34^{cdc2/cyclin\ B}$ --

Column 15,
Lines 24-25, "due the lack" should read -- due to the lack --

Column 16,
Line 43, "calorimetric" should read -- colorimetric --
Line 48, "absorbence" should read -- absorbance --
Line 53, "that the lose of" should read -- that the loss of --
Line 54, after "incorporation" insert -- , --

UNITED STATES PATENT AND TRADEMARK OFFICE
CERTIFICATE OF CORRECTION

PATENT NO. : 6,214,821 B1
DATED : April 10, 2001
INVENTOR(S) : S.S. Daoud

It is certified that error appears in the above-identified patent and that said Letters Patent is hereby corrected as shown below:

Column 18,
Line 23, "6: 83:92" should read -- 6: 83-92 --

Column 19,
Line 61, "$t_{1/2}\alpha$ and the $t_{1/2}\beta$" should read -- $t_{1/2\alpha}$ and the $t_{1/2\beta}$ --

Column 20,
Line 15, "On hour" should read -- One hour --
Lines 62-63, "when used in combine" should read -- when used in combination --
Line 63, "FIG. 14, depicts a" should read -- FIG. 14 depicts --

Column 21,
Line 9, "peak height were" should read -- peak heights were --

Column 24,
Line 6, "6:83:92" should read -- 6:83-92 --
Line 15, "comprising an enhanced effective amounts of" should read -- comprising an enhanced effective amount of --
Lines 28-29, "function comprising an enhanced effective amounts of contacting the cells with a composition" should read -- function comprising contacting the cells with an enhanced effective amount of a composition --
Line 41, "patient an enhanced effective amounts of" should read -- patient an enhanced effective amount of --
Line 44, "9-aminocamiptothecin;" should read -- 9-aminocamptothecin; --

Signed and Sealed this

Twenty-sixth Day of August, 2003

JAMES E. ROGAN
*Director of the United States Patent and Trademark Office*